US009890424B2

(12) United States Patent
Schultz et al.

(10) Patent No.: US 9,890,424 B2
(45) Date of Patent: Feb. 13, 2018

(54) SEQUENCING DEVICE

(71) Applicant: LIFE TECHNOLOGIES CORPORATION, Carlsbad, CA (US)

(72) Inventors: Jonathan Schultz, Guilford, CT (US); Todd Roswech, Guilford, CT (US); Jon A. Hoshizaki, Cupertino, CA (US); Albert L. Carrillo, South San Francisco, CA (US); James A. Ball, Ledyard, CT (US)

(73) Assignee: Life Technologies Corporation, Carlsbad, CA (US)

( * ) Notice: Subject to any disclaimer, the term of this patent is extended or adjusted under 35 U.S.C. 154(b) by 138 days.

(21) Appl. No.: 14/742,404

(22) Filed: Jun. 17, 2015

(65) Prior Publication Data

US 2015/0361488 A1    Dec. 17, 2015

Related U.S. Application Data

(60) Provisional application No. 62/013,475, filed on Jun. 17, 2014.

(51) Int. Cl.
*C12Q 1/68*   (2006.01)
*G01N 35/10*  (2006.01)
(Continued)

(52) U.S. Cl.
CPC .......... *C12Q 1/6869* (2013.01); *B01F 1/0027* (2013.01); *B01F 5/0683* (2013.01);
(Continued)

(58) Field of Classification Search
CPC  B01F 11/0048; B01F 11/0071; B01F 1/0027; B01F 5/0683; B01L 2200/04;
(Continued)

(56) References Cited

U.S. PATENT DOCUMENTS 5,411,876 A    5/1995  Bloch et al.
8,546,128 B2*  10/2013  Schultz ............. B01L 3/502738
                                              422/502
(Continued)

FOREIGN PATENT DOCUMENTS

WO    2007/106579    9/2007
WO    2012/006185    1/2012
(Continued)

OTHER PUBLICATIONS

Partial International Search Report of the International Searching Authority for International Application No. PCT/US2015/036277 dated Sep. 21, 2015, 8 pages.
(Continued)

*Primary Examiner* — Maureen Wallenhorst

(57) ABSTRACT

A method of preparing reagents includes inserting a cartridge into an instrument. The cartridge includes a plurality of reagent enclosures disposed in a cavity of the cartridge and exposing a port to an exterior of the cartridge. Each reagent enclosure includes a reagent container including a reagent and an internal cavity defining a compressible volume, an opening defined through the reagent container to the internal cavity. The method further includes connecting a plurality of fluid ports to the openings of the plurality of reagent enclosures; applying a solution through the fluid ports to at least partially fill the plurality of reagent enclosures; and cycling a pressure of the cavity, whereby for each of the reagent enclosures, during increasing pressure, the solution enters the internal cavity of the reagent container, combines with the reagent, and compresses the compressible volume, and during decreasing pressure, the compressible volume decreases and the reagent is ejected through the opening.

10 Claims, 22 Drawing Sheets

(51) Int. Cl.
| | |
|---|---|
| *G01N 1/00* | (2006.01) |
| *B01F 5/06* | (2006.01) |
| *B01F 11/00* | (2006.01) |
| *B01F 1/00* | (2006.01) |
| *B01L 3/00* | (2006.01) |
| *G01N 27/414* | (2006.01) |

(52) U.S. Cl.
CPC ...... *B01F 11/0048* (2013.01); *B01F 11/0071* (2013.01); *B01L 3/502* (2013.01); *B01L 3/527* (2013.01); *C12Q 1/6806* (2013.01); *G01N 27/4145* (2013.01); *G01N 35/1002* (2013.01); *G01N 35/1095* (2013.01); *B01L 3/505* (2013.01); *B01L 3/563* (2013.01); *B01L 2200/04* (2013.01); *B01L 2200/16* (2013.01); *B01L 2300/022* (2013.01); *B01L 2300/0681* (2013.01); *B01L 2300/0861* (2013.01); *B01L 2300/123* (2013.01); *B01L 2400/0481* (2013.01); *B01L 2400/0487* (2013.01); *B01L 2400/0655* (2013.01); *B01L 2400/0683* (2013.01); *Y10T 436/11* (2015.01); *Y10T 436/143333* (2015.01)

(58) Field of Classification Search
CPC .......... B01L 2200/16; B01L 2300/022; B01L 2300/0681; B01L 2300/0861; B01L 2300/123; B01L 2400/0481; B01L 2400/0487; B01L 2400/0655; B01L 2400/0683; B01L 3/502; B01L 3/505; B01L 3/527; B01L 3/563; C12Q 1/6806; C12Q 1/6869; G01N 27/4145; G01N 35/1002; G01N 35/1095; Y10T 436/11; Y10T 436/143333; Y10T 436/204998; Y10T 436/2575
USPC ..... 436/43, 94, 133, 148, 180; 422/63, 68.1, 422/82.13, 509; 435/287.2, 287.3; 506/6, 27
See application file for complete search history.

(56) References Cited

U.S. PATENT DOCUMENTS

| | | | |
|---|---|---|---|
| 9,375,716 B2* | 6/2016 | Schultz | .................. B01L 3/567 |
| 2006/0141486 A1* | 6/2006 | Coonan | ................. B01L 3/5085 435/6.11 |
| 2009/0282932 A1* | 11/2009 | Blackwell | .......... G01N 35/1002 73/863.21 |
| 2012/0076692 A1 | 3/2012 | Miraghaie | |

FOREIGN PATENT DOCUMENTS

| | | |
|---|---|---|
| WO | 2012/151473 | 11/2012 |
| WO | 2015/195831 | 12/2015 |

OTHER PUBLICATIONS

International Search Report and Written Opinion of the International Searching Authority for International Application No. PCT/US2015/036277 dated Nov. 30, 2015, 23 pages.
PCT/US2015/036277, International Preliminary Report on Patentability dated Dec. 29, 2016, 17 pp.

* cited by examiner

SEQUENCING DEVICE

CROSS-REFERENCE TO RELATED APPLICATION(S)

This application claims benefit of U.S. Provisional Application No. 62/013,475, filed Jun. 17, 2014, which is incorporated herein by reference in its entirety.

FIELD OF THE DISCLOSURE

This disclosure, in general, relates to improved sequencing devices.

BACKGROUND

Increasingly, biological and medical research is turning to sequencing for enhancing biological studies and medicine. For example, biologist and zoologist are turning to sequencing to study the migration of animals, the evolution of species, and the origins of traits. The medical community is turned sequencing for studying the origins of disease, sensitivity to medicines, and the origins of infection. But, sequencing has historically been an expensive process, thus limiting its practice.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1:
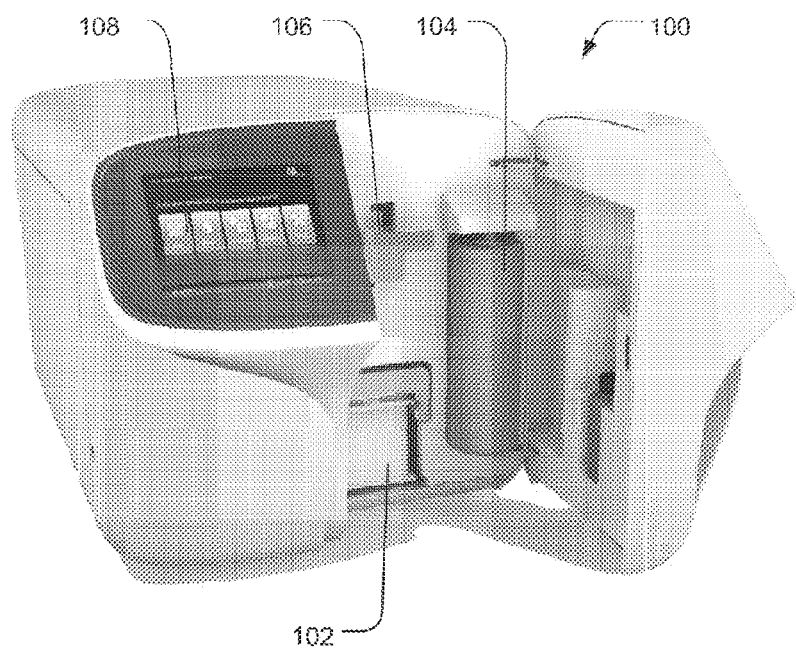
FIG. 1 includes an illustration of an example sequencing instrument.

In an exemplary embodiment, a sequencing system includes an instrument to receive a semiconductor sequencing chip and to carry out processes that result in the identification of a sequence of bases. In particular, the instrument can receive a reagent cartridge, wash solutions and a semiconductor sequencing chip. The instrument can include a user interface, such as a touchscreen user interface, and can include computational circuitry and controllers to control the delivery of reagents and wash solution to the semiconductor sequencing chip, as well as the acquisition of data from the semiconductor sequencing chip to facilitate identification of the sequence of bases.

An exemplary instrument includes a reagent cartridge receptacle, a further receptacle for receiving a wash buffer cartridge, and a chip clamp for receiving a semiconductor sequencing chip. In addition, the instrument includes a touchscreen user interface. Such an instrument provides for limited sequencer touch points, no compressed gas utilization (instead utilizing a closed pump-driven system), no high-quality water utilization, easy operation (including an intuitive graphical user interface, plug-and-play consumables, etc.), fast single day runtimes, integrated onboard computing for primary data analysis, dual-mode operation in a research use only (RUO) or diagnostic mode (Dx), small benchtop footprint, scalability (upgradable chassis for different performance levels) or a low-cost, or any combination thereof.

In particular, the instrument can include a compressor for providing internally generated gas pressure. Reagents can be provided in a preloaded cartridge to limit user interaction with reagent preparation. Similarly, wash solutions can be provided as a plug-and-play wash solution, such as within a cartridge. In an example, the pH of the wash solution can be stabilized using a solid-state buffer.

Flow rates of reagents within the system can be controlled for example using dynamic flow control using a pinch valve regulator. The system can also include a cleaning solution that performs automatic post-run washing. The instrument may include an internal server for processing data received from the semiconductor sequencing chip. Alternatively, or in addition, the system can provide an output data port to connect an external server for processing the data. Furthermore, the internal computational systems can be configurable and upgradable.

The system can utilize pressure driven liquid flow using an internal gas supply, without the use of external gas supplies. In particular, a reagent cartridge system can utilize liquid or lyophilized nucleotides within separate enclosures or bags. The enclosure can be deflated of any initial air content by pressurizing the chamber external to the bags and flowing air from the bags to waste. The wash solution can be applied into the bags. Residual air bubbles can rise to the top and can purge to waste. Mixing is accomplished by pressurizing and rapidly depressurizing the chamber external to the bags, causing the liquid in the bags to pressurizing and depressurized. The liquid or lyophilized nucleotides are contained within the mixer (reagent container) that in response to depressurization expels the solution including nucleotides, causing a mixing of the nucleotide within the bag.

As external gas pressure is applied to the bag enclosure, internal wash solution flows into the mixer and an internal compressible volume within the mixer compresses. When the gas pressure external to the bag is quickly released, the pressure charged within the compressible volume forces the wash solution out through nozzles at high velocity, mixing the liquid including nucleotides within the bag.

When applying flow through a flow cell of the semiconductor sequencing chip, dynamic flow control can be accomplished by utilizing a pinch flow regulator (pinch valve regulator). Such a dynamic flow control reduces the use of resistance tubing coils and reduces the potential for clogging. Flow rates can be programmable and can be adjusted by adjusting a control pressure within the pinch flow regulator.

The system can utilize a solid-state buffering system, such as a ceramic buffering system, for example, particulate titanium dioxide. The wash solution reagent can be provided in a single use bottle that is readily mixed. The solution can include a solid-state buffer, eliminating auto pH routines, and providing long-term pH stability. The particulate titanium dioxide can be easily confined to the bottle by a filter, thus limiting the particulate within the system. In addition, the primary wash bottle can utilize packaging that has low permeability to gas and thus is low permeability to acidifying $CO_2$. The container may also be shipped with a $CO_2$ absorbent packet, to further limit exposure to carbon dioxide.

The semiconductor sequencing chip can be received in a chip clamp that loads the chip in the system and connects the chip to the fluidics system. The chip clamp can include an integrated squid valve manifold and removes tubing connections. The chip clamp can further include reference electrodes, integrated chip temperature control, and integrated manifold heating.

The instrument can further rely on a reagent cartridge, limiting contact and processing by users. The simple cartridge is loaded and includes five containers or enclosures (for nucleotide and a bead find or pH-adjusting reagent). The cartridge can also include a charging port to quickly pressurize/depressurize the cartridge utilizing an exhaust valve, for example on a manifold connecting to the reagent cartridge. Optionally, a silencer is applied on the exhaust to reduce noise associated with a quick depressurizing the cartridge.

The instrument further includes electronics that are scalable and configurable. In particular, computing power and memory can be exchanged. The system can further include support for RFID tags, for example, on semiconductor sequencing chips or cartridges.

An exemplary reagent cartridge can include color-coded ports for different nucleotide solutions and a bead find or pH adjusting solution. In addition, the reagent cartridge can include input and output ports for a $CO_2$ scrubber. The cartridge can also be provided with an RFID tag that identifies, for example, lot numbers and expiration dates.

The cartridge can include individualized chambers into which reagent containers are applied or the $CO_2$ scrubber is inserted. The reagent containers are inserted through the cartridge lid into reagent pouches or enclosures secured to the lid within the cartridge.

For exemplary reagent cartridge manufacturing, fittings are applied into pouches, for example, including a low-density polyethylene/poly ethylene terephthalate film. The cartridge base, lid, port gaskets, and other parts are then assembled applying the pouches to the lid, followed by the lid to the base, as well as the insertion of gaskets into the lid. A reagent container includes a mixer body into which a foam member is inserted. A mixer cap is applied to the mixer body. In an example, the mixer cap can include lyophilized reagent or liquid reagent. In another example, the reagent can be frozen or stored within porous ceramic or polymeric foam. The assembled reagent mixers and scrubbers can then be applied to the reagent cartridge assembly. RFID tags can be applied to the cartridge, and the cartridge can be boxed and stored for shipping.

Reagent can be applied in to the mixer or cartridges either in a lyophilized form or as a frozen liquid form. In an example, lyophilized nucleotide pellets can be formed and then inserted into the mixers. In another example nucleotides can be dried onto filter paper that is integrated into bug mixers. In another example, nucleotides can be dried directly onto compressible foam or within the caps (second portions) of the mixer (reagent containers).

In an example, FIG. 1 includes an illustration of exemplary instrument 100 for sequencing. The instrument 100 can include a connector to receive a container of buffered solution 104, a clamp 106 to receive a sequencing device, and a manifold to receive a reagent cartridge 102. Further, the sequencing instrument 100 includes computational circuitry to control fluid flow, data retrieval from the sequencing device, interpretation of the data, and a user interface 108. In a particular example, the sequencing device is a pH or ion sensitive device, for example, including a plurality of ion sensitive field effect transistors (ISFETs).

Figure 25:
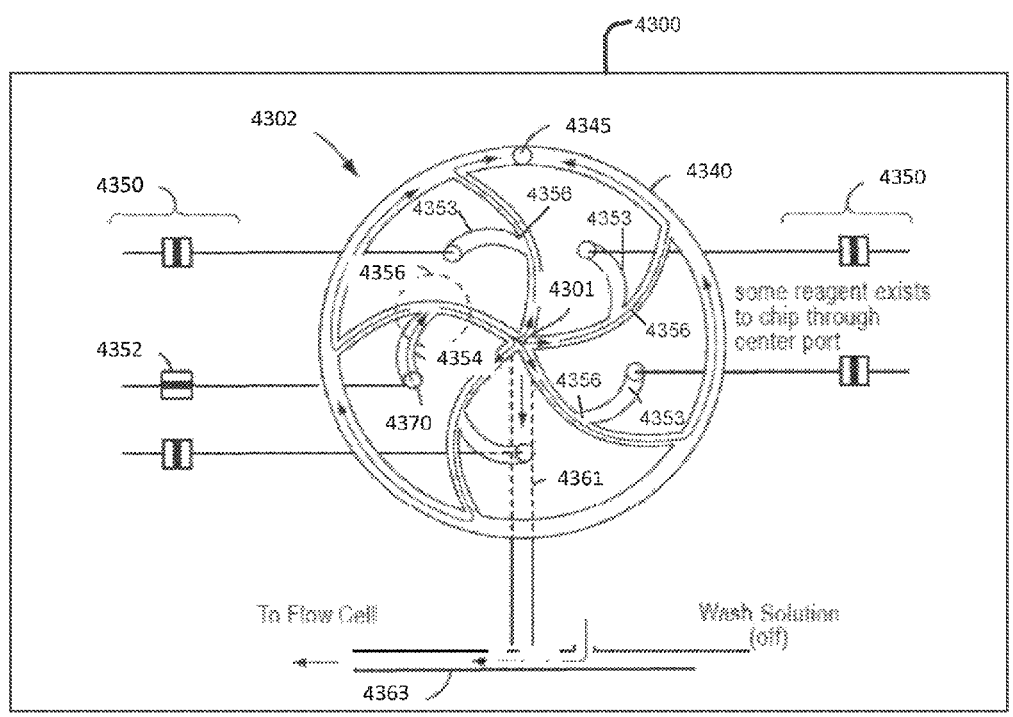
FIG. 25 includes an illustration of an example fluidic circuit.

In a particular example, the sequencing instrument includes circuitry to control fluid flow within the system. In an example illustrated in FIG. 2, the instrument 200 includes connections to a cartridge 202. Reagent can flow from the cartridge 202 through a fluidic circuit 204 and to a sequencing device 206. Fluid passing through the fluidic circuit 204 can optionally be directed to a waste container 212 or through the sequencing device 206 to a waste container 210 through pinch flow regulators 208 or 230. In an alternative example, a single waste container can take the place of waste containers 210 or 212. An exemplary embodiment of a cartridge 202 is illustrated in FIGS. 12-16. An exemplary embodiment of a pinch flow regulator is illustrated FIGS. 19-22. An exemplary fluidic circuit is illustrated in FIG. 3 and FIG. 25.

As further described below, a solution in a container 226, such as a buffered solution, can flow through a valve 228 and be used to prepare reagent solutions in reagent enclosures 214. The reagent solutions 214 can selectively flow to the fluidic circuit 204 and to the sequencing device 206 or waste containers 210 or 212. The solution in the solution container 226 can optionally flow through valve 232 to the fluidic circuit 204 and can act as a wash solution, washing the fluidic circuit 204 and optionally the sequencing device 206 of reagents from the reagent solutions. The buffered solution in the solution container 226 can optionally be pumped in the system. Alternatively, the buffered solution can be driven by pressure, for example, supplied using air through inlet 234.

In an example, the system 200 can include a compressor 216 that compresses gas or air to flow through a scrubber cartridge 220, optionally included in the reagent cartridge 202. For example, the scrubber cartridge 220 can include components, such as soda lime, to remove carbon dioxide from air. Receptacle 218 can be used to store and supply pressurized air to the system. For example, the pressurized air can be used to pressurize the solution container 226. In another example, the pressurized air can be supplied to the cavity of the cartridge 202 to pressurize the reagent enclosures 214 and drive reagent solutions selectively through the valves 222 to the fluidic circuit 204. In a further example, the compressed air from the receptacle 218 can be used to clean a fluidic circuit 204 through valve 224. The pressurized air can drive remaining liquids within the fluidic circuit 204 to the waste container 212, through the sequencing device 206 to the waste container 210, or back through valves 222 to the reagent enclosures 214.

Figure 3:
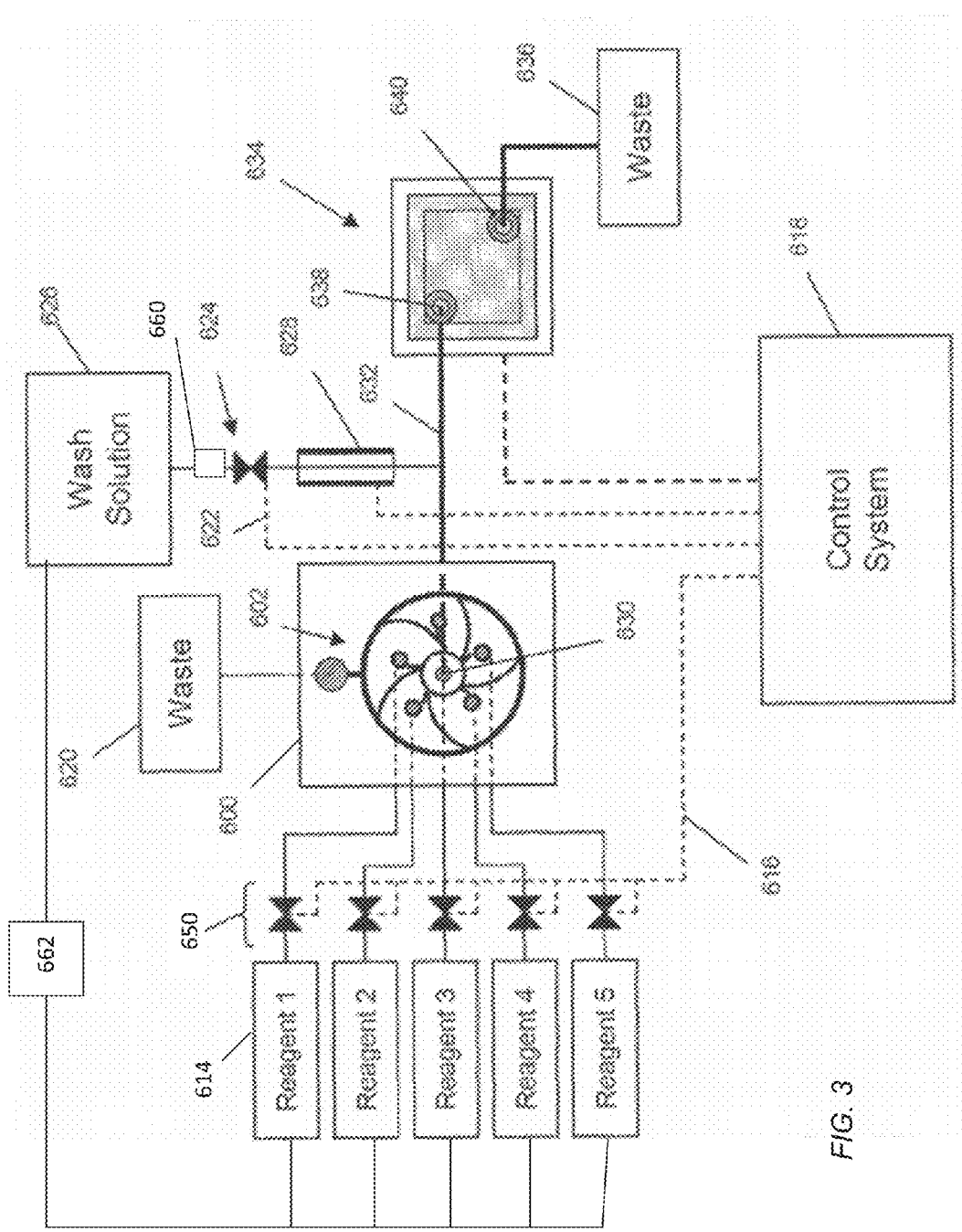
FIG. 3 includes a schematic of an example sequencing instrument.

FIG. 3 includes an illustration of a more detailed embodiment of the fluidic circuit. FIG. 3 diagrammatically illustrates a system employing an enclosure 614 that is a reagent reservoir, for example, for carrying out pH-based nucleic acid sequencing. Each electronic sensor of the apparatus generates an output signal. The fluid circuit permits multiple reagents to be delivered to the reaction chambers.

In FIG. 3, the system includes a fluidics circuit 602 connected to the reagent reservoirs 614, to a waste reservoir 620, and to a biosensor 634 by fluid pathway 632 that connects fluidics node 630 to inlet 638 of biosensor 634 for fluidic communication. The prepared and mixed reagent solution from reservoirs 614 can be driven to fluidic circuit 602 by a variety of methods including pressure, pumps, such as syringe pumps, gravity feed, and the like, and are selected by control of valves 650. Reagents from the fluidics circuit 602 can be driven to the waste containers 620 and 636. The control system 618 includes controllers for valves 650 that generate signals for opening and closing via an electrical connection 616.

The control system 618 also includes controllers for other components of the system, such as a wash solution valve 624 connected thereto by the electrical connection 622, and the reference electrode 628. The control system 618 can also include control and data acquisition functions for the biosensor 634. In one mode of operation, the fluidic circuit 602 delivers a sequence of selected reagents 1, 2, 3, 4, or 5 to the biosensor 634 under programmed control of the control system 618, such that in between selected reagent flows, the fluidics circuit 602 is primed and washed with a wash solution 626, and the biosensor 634 is washed with the wash solution 626. Fluids entering the biosensor 634 exit through the outlet 640 and are deposited in the waste container 636. A similar setup may be used for optical sequencing systems, with photodiodes or CCD cameras, for example.

In a particular example, the wash solution 626 can be a buffered suspension including the solid buffer particulate. The buffer suspension (wash solution) can be filtered using a filter 660 before entering the fluidics circuit 602 or sensor 634. In a further example, the buffered suspension can be applied to the reagent reservoirs 614 through filter 662 to form the reagent solutions from reagent concentrate within the reagent reservoirs. Alternatively, the filter 660 and 662 can be the same filter. In an example, the reagent concentrate is a liquid concentrate. In another example, the reagent concentrate is a dried concentrate, such as a lyophilized reagent (e.g., lyophilized nucleotides). Alternatively, the illustrated filters 660 and 662 can be combined. In another example, filters can be located downstream of the reagent reservoirs 614, such as between the reagent reservoirs 614 and the valves 650.

Figure 4:
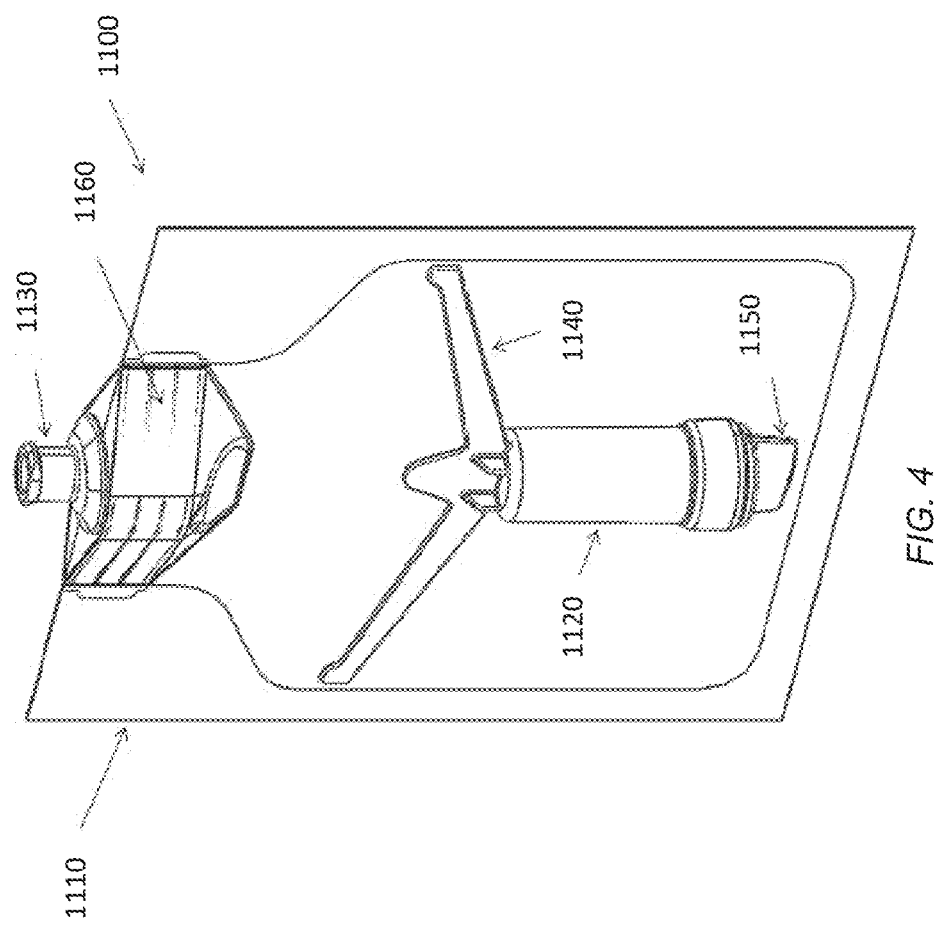
FIG. 4 is a perspective view describing an exemplary reagent storage apparatus.

FIG. 4 is a perspective view describing an exemplary reagent storage apparatus 1100. In an example, the reagent storage apparatus 100 can include an enclosure 1110. A container 1120 is disposed within the enclosure 1110. In an example, the enclosure 1110 can be a flexible enclosure. A flexible enclosure, such as a sealable flexible bag enclosure, can be pressurized and depressurized by externally applying pressure, such by applying pressurized gas to the external surfaces of the flexible enclosure. Alternatively, the enclosure can be rigid so that externally applied gas pressure does not readily translate to pressure of fluid within the enclosure 1110.

The reagent storage apparatus 1100 can also include a fluid port 1130 coupled to a fitting 1160 attached to the enclosure 1110 to provide fluid access to the interior of the enclosure 1110. The fluid port 1130 can be coupled to the fitting 1160 to seal the enclosure 1110 from an exterior environment after insertion of the container 1120. The enclosure 1110 can be, for example, thermosealed to itself and the fitting 1160, except where otherwise sealed by the fluid port 1130.

The container 1120 can include one or more arms 1140 and a flange 1150. The arms 1140 can position the container 1120 within the enclosure 1110, such as approximately centrally, to disperse a reagent within the enclosure 1100 evenly. The flange 1150 can be provided for convenient assembly of the container 1120. In an example, the arm 1140 is flexible. For example, the arm 1140 can be formed of wire or a polymeric material. Alternatively, the arm 1140 can be rigid. Alternatively, the arm 1140 and the flange 1150 are not limited to those illustrated in FIG. 4 and can include a structure that positions the container within a predetermined location or orientation within the enclosure 1110. The container 1120 can be directly or indirectly connected to the fluid port 1130 or alternatively positioned a suitable distance away from the fluid port 1130 as show in FIG. 4. The sealed enclosure 1100 including the enclosure 1110 and container 1120 provides simplified storage and transportation of a reagent within the container 1120.

Figure 5:
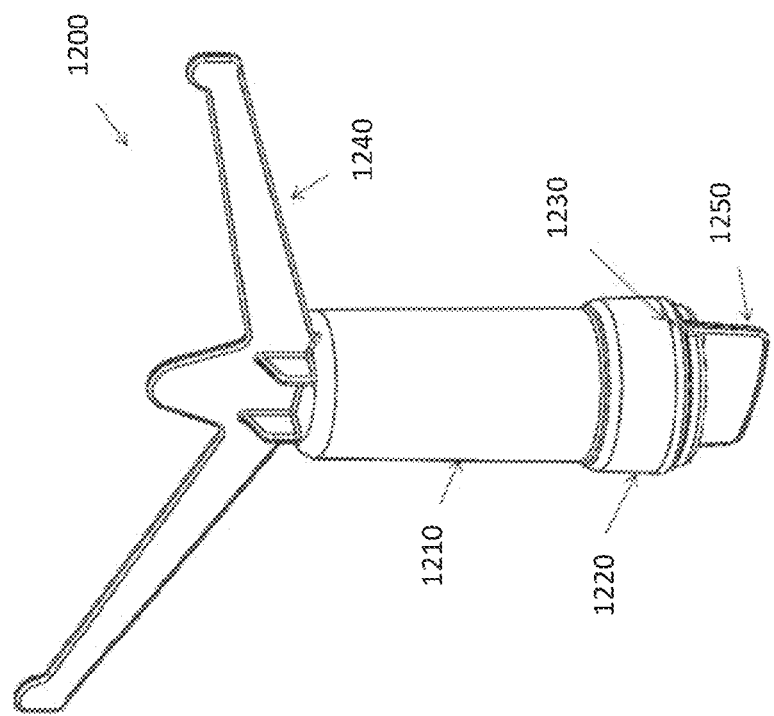
FIG. 5 is a perspective view describing an example container.

FIG. 5 is a perspective view describing an example container 1200. The container 1200 can include a first portion 1210 and a second portion 1220 coupled to the first portion 1210. Elements such as an optional compressible member and a reagent can be inserted within the container 1200 prior to connecting the first portion 1210 to the second portion 1220. In an example, the second portion 1220 can be a cap that slides over or otherwise covers part of the first portion 1210 to form the internal cavity. In another example, the second portion 1220 can be an insert that slides into the first portion 1210. The second portion 1220 can be connected to the first portion 1210 by any suitable attachment mechanism including screwing the second portion 1220 onto the first portion 1210 or vice versa, a locking mechanism, adhesive, or any other suitable attachment mechanism.

In an example, the internal cavity defines a compressible volume. The compressible volume compresses in response to fluid pressure and does not dissipate or leave the internal cavity of the container 1200. The compressible volume can include a compressible gas volume or can be a compressible member, such as a resilient polymer or foam.

The container 1200 can define a passage 1230 providing fluidic communication between an internal cavity of the container 1200 and an exterior of the container 1200. In an example, one or more passages 1230 can be defined through to the internal cavity. Such passages 1230 can be drilled through the first or second portions of the container 1200. In another example, the second portion 1220 can include the passage 1230 or can include a slot extending beyond a region at which the second portion 1220 engages the first portion 1210, thus forming the passage 1230.

One or more arms 1240 can be coupled to the first portion 1210 to position the container 1200 as desired within an enclosure. A flange 1250 can be coupled to the second portion 1220 to assist with applying the second portion 1220 to the first portion 1210 or to position the container 1200 away from a bottom of the enclosure.

Figure 6:
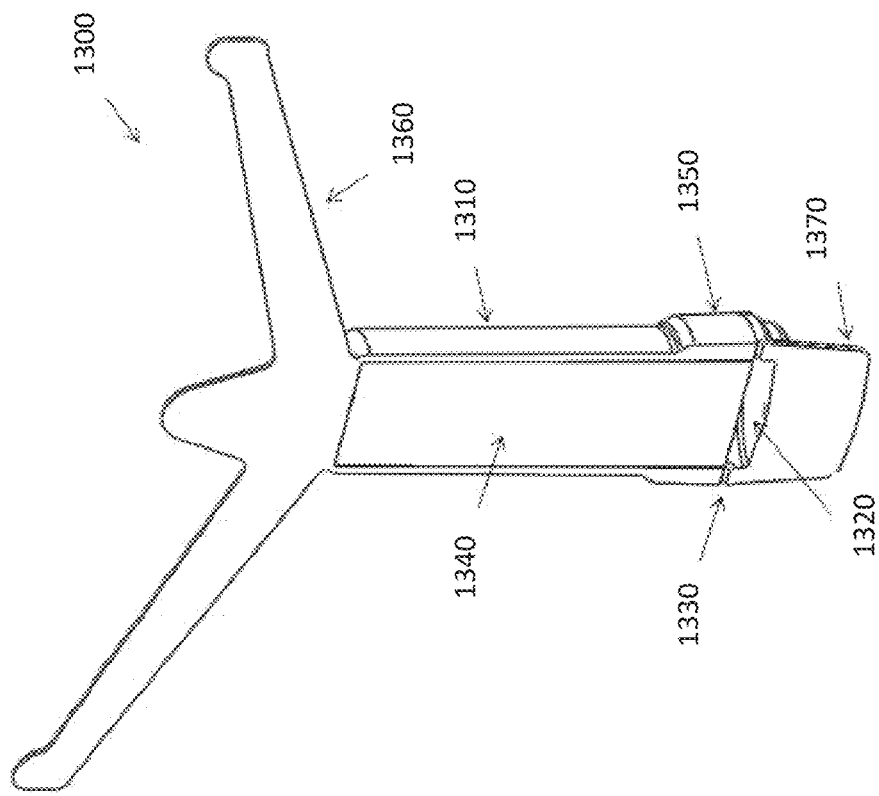
FIG. 6 is a cross-sectional perspective view describing an example container.

FIG. 6 is a cross-sectional perspective view describing an example container 1300. The container 1300 defines an internal cavity 1320 and defines a passage 1330 providing fluidic communication between the internal cavity 1320 and the exterior of the container 1300. The passage 1330 can be drilled through the container 1300. In another example, a cap or insert can include a slot that extends beyond a region engaging the container 1300 and that forms the passage 1330. The container 1300 can include a first portion 1310 and a second portion 1350 coupled to the first portion 1310 that allows elements such as a compressible member 1340 and reagent to be inserted into the internal cavity 1320 of the container 1300.

The internal cavity 1320 defines a compressible volume. The compressible volume is a volume that compresses in response to pressure to match the pressure, and can expand in response to depressuring, providing a counter force on fluid pressure. In an example, the compressible volume includes a compressible gas that compresses to match the pressure of fluid entering the internal volume without dissipating or exiting the internal cavity and in response to a depressurization of the fluid pushes the fluid out of the internal cavity 1320. Optionally, the compressible volume can include a compressible member 1340. The compressible member 1340 is compressible under pressurization and upon depressurization, substantially returns to its previous form. For example, the compressible member 1340 can be a foam material. In particular, the compressible member 1340 can be a closed-cell foam of elastomeric material. In an example, the compressible member can include polyurethane foam.

In an example, the reagent can be disposed within the second portion 1350. The reagent can be a lyophilized nucleotide or an analog thereof. In another example, the reagent is a solution absorbed on a porous metal, ceramic, or polymeric sponge-like material or frit. Optionally, the reagent solution can be frozen. In an alternative example, the reagent can include a pH-adjusting reagent, such as an acid or base.

One or more arms 1360 can be coupled to the first portion 1310 to position the container 1300 as desired within an enclosure. A flange 1370 or other suitable appendage can be coupled to the second portion 1350 to assist with engaging the second portion 1350 with the first portion 1310 or to position the container 1300 within the enclosure.

Figure 7:
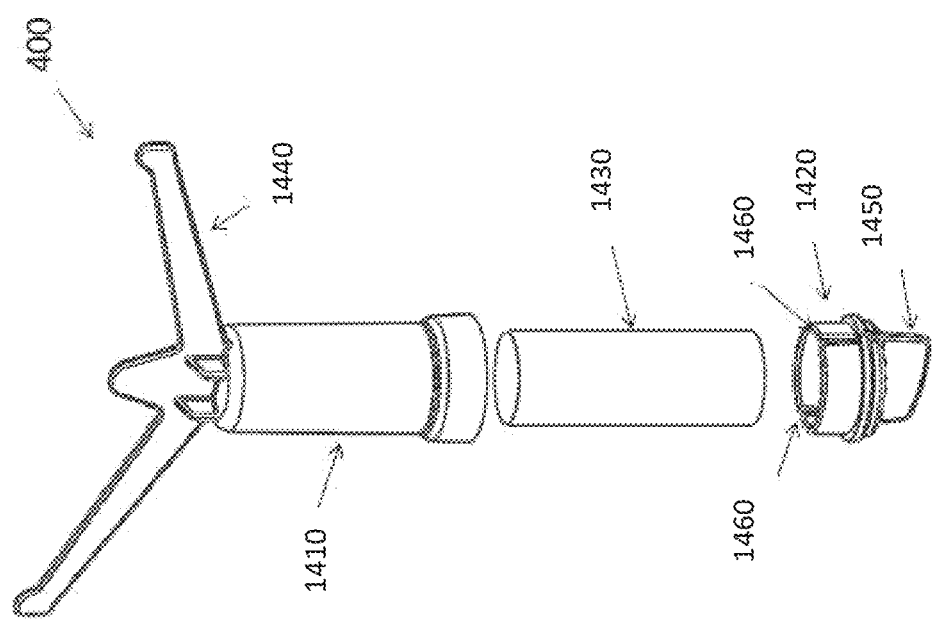
FIG. 7 is an exploded schematic view describing an example container.

FIG. 7 is an exploded schematic view describing an example container 1400. The container 1400 can include a first portion 1410 and a second portion 1420 (e.g., an insert) coupled to the first portion 1410, allowing elements such as an optional compressible member 1430 to be inserted within the container 1400. The second portion 1420 can be secured to the first portion 1410 by sliding or screwing into the first portion 1410. One or more flexible arms 1440 can be coupled to the first portion 1410 to position the container 1400 within an enclosure. A flange 1450 can be coupled to the second portion 1420 to assist with engaging the second portion 1420 and the first portion 1410 or to position the container 1400 within the enclosure.

In an example, the second portion 1420 can define one or more slots 1460. The first portion 1410 and the second portion 1420 can engage so as to leave a portion of the one or more slots 1460 exposed, providing one or more passages between the internal cavity of the container 1400 and the exterior of the container 1400.

Figure 8:
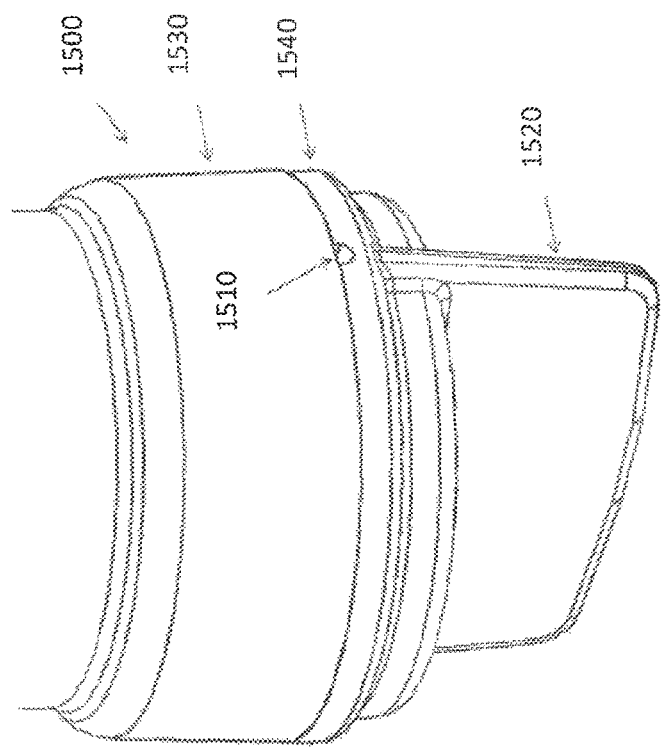
FIG. 8 is a detailed perspective view describing an example container.

FIG. 8 is a detailed perspective view describing an example container 1500. The detailed view of the container 1500 can define a passage 1510 providing fluidic communication between an internal cavity of the container 1500 and an exterior of the container 1500. An end of the container 1500 includes a fitting 1530 to receive an insert 1540. The insert 1540 includes a hole or slot not covered when the insert 1540 is applied to the fitting, forming the passage 1510. Alternatively, the insert 1540 can include a hole, notch, mesh, pores or any other suitable feature for providing fluid communication to the fitting 1530. A flange 1520 can be coupled to the container 1500 to allow control of the insert 1540 as it is applied to the fitting 1530 and to position the container within an enclosure.

Figure 9:
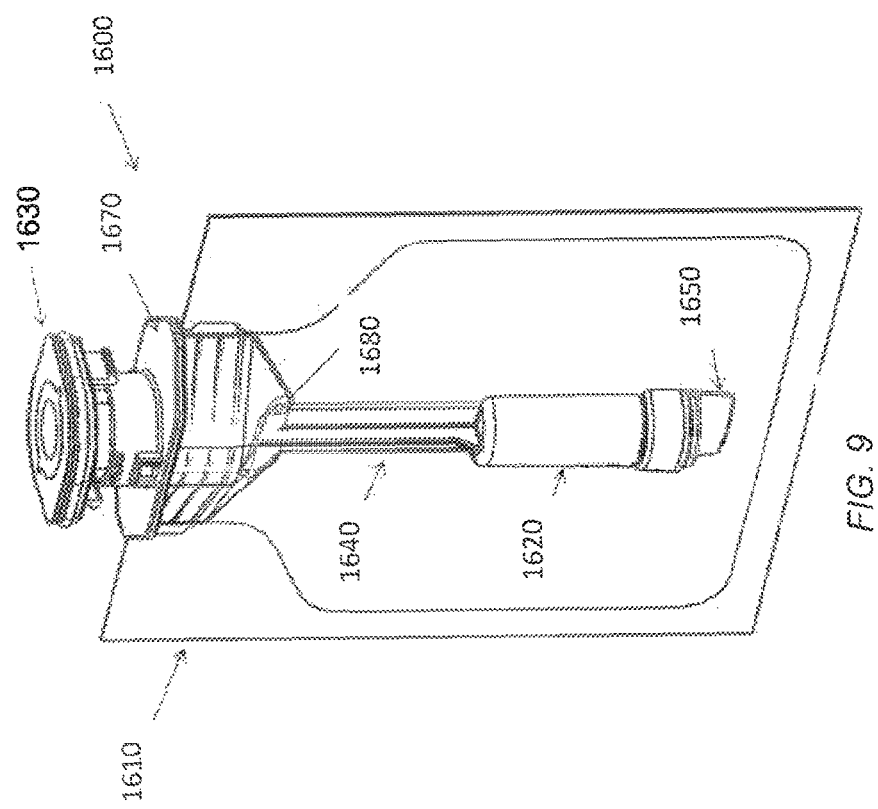
FIG. 9 is a perspective view describing an exemplary reagent storage apparatus.

FIG. 9 is a perspective view describing an exemplary reagent storage apparatus 1600. The reagent storage apparatus 1600 includes an enclosure 1610. A container 1620 is disposed within the enclosure 1610. The enclosure 1610 can be a flexible enclosure as described above. For example, the flexible enclosure can be a sealable flexible bag enclosure that can be pressurized and depressurized externally via fluid pressure or gas pressure. Alternatively, the enclosure 1610 can be a rigid enclosure. The enclosure 1610 can sealably engage a seal structure 1670, such as a fitting, having a bore 1680, such as a central bore. The container 1620 can be coupled to an arm 1640, which can be coupled to a fluid port 1630, and inserted through the bore 1680 of the fitting 1670.

The fluid port 1630 provides fluid access to the interior of the enclosure 1610 through the bore 1680. The fluid port 1630 can be coupled to the seal structure or fitting 1670 of the reagent storage apparatus 1600 from an exterior environment after inserting the container 1620. The arm 1640 couples the container 1620 to the fluid port 1630 to position the container 1620, for example, approximately centrally within the enclosure 1610 to disperse a reagent within the enclosure 1610 evenly. The arm 1640, the container 1620, and the fluid port 1630 can be a single integrated piece. In an example fluid flows through the fluid port 1630 and through the bore 1680 of the fitting 1670 into the enclosure 1610, optionally along the arm 1640. The arm 1640 can position the container 1620 with or without a flange 1650.

Figure 10:
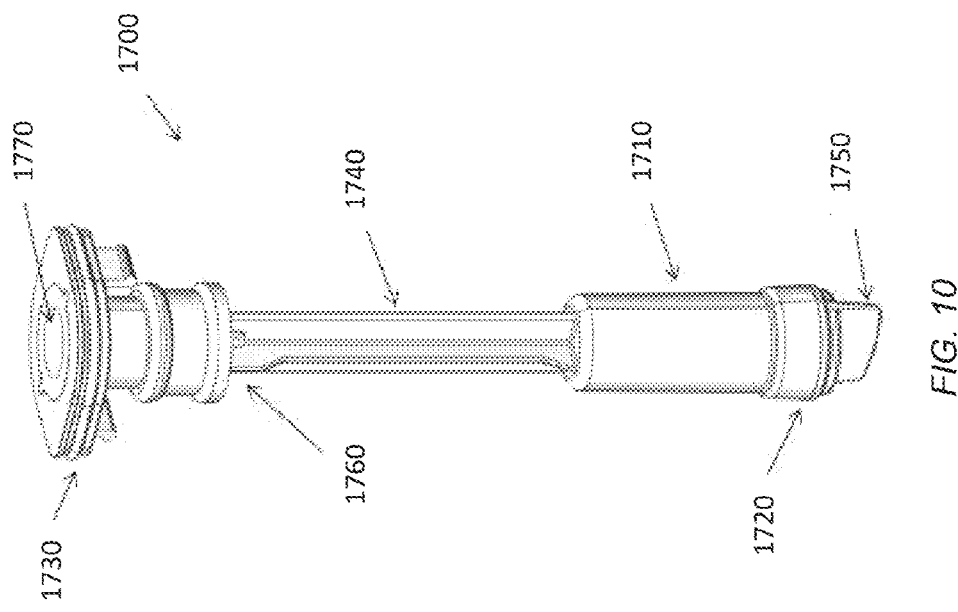
FIG. 10 is a perspective view describing an example container.

FIG. 10 is a perspective view describing an example container 1700. The container 1700 can include a first portion 1710 and a second portion 1720 coupled to the first portion 1710 allowing elements such as an optional compressible member to be inserted within the container 1700. A fluid port 1730 is coupled to the container 1700 and provides fluid access to an enclosure into which the container 1700 is inserted. An arm 1740 can coupled the first portion 1710 and the fluid port 1730 to position the container 1700 within an enclosure.

In an example, the second portion 1720 is an insert to engage the first portion 1710. In another example, the second portion 1720 forms a cap to cover an end of the first portion 1710. Fluid can flow through the opening 1770 of the port 1730 and to an opening 1760 along the arm 1740. The fluid port can include a gasket to facilitate sealing. A flange 1750 can be coupled to the second portion 1720.

Figure 11:
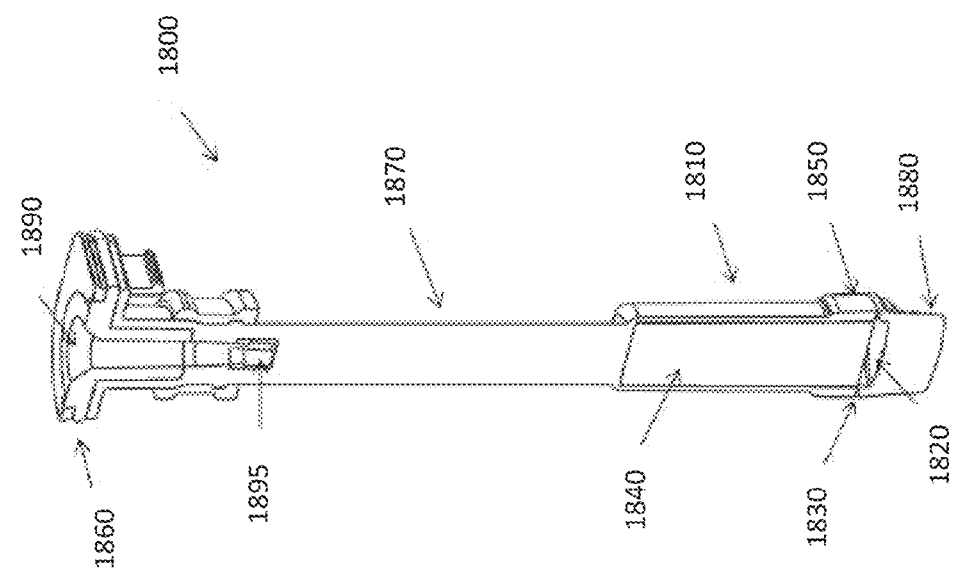
FIG. 11 is a cross-sectional perspective view describing an example container.

FIG. 11 is a cross-sectional perspective view describing an example container 1800. The container 1800 defines an internal cavity 1820 and defines a passage 1830 providing fluidic communication between the internal cavity 1820 and the exterior of the container 1800. The container 1800 can include a first portion 1810 and a second portion 1850 coupled to the first portion 1810 defining a compressible volume. In an example, elements, such as a compressible member 1840 and reagent, can be inserted into the internal cavity 1820 of the container 1800.

In an example, the second portion 1850 is a cap to apply over an end of the first portion 1810. In another example, the second portion 1850 is an insert to apply to a fitting of the first portion 1810. In an example, a passage 1830 is formed in the second portion 1850, for example, as a hole or a slot.

The reagent can be disposed within the second portion 1850. The reagent can be a lyophilized nucleotide or an analog thereof. In another example, the reagent can be a nucleotide solution absorbed by a porous metallic, ceramic or polymeric sponge or frit. In a further example, the reagent can be frozen. In an additional example, the reagent can include a pH-adjusting reagent, such as an acid or a base.

A fluid port 1860 is coupled to the container 1800 and provides fluid access to an enclosure in which the container 1800 is inserted. For example, fluid entering opening 1890 can pass through passages 1895 and into an enclosure. An arm 1840 can be coupled to the first portion 1810 and the fluid port 1860. A flange 1880 can be coupled to the second portion 1850 to also position the container 1800 within the enclosure.

The reagent storage apparatus can be inserted into a case or cartridge having a cavity. In an example, pressure can be varied within the cavity to change the pressure of liquid within the flexible enclosure and thus, influence the pressure within the container. Alternatively, pressure can be applied through the opening 1890 and internal to the enclosure. In an example, one or more of the enclosures can be incorporated into the case. The case can define one or more pressure chambers in which pressure can be applied and relieved from the enclosures.

Figure 12:
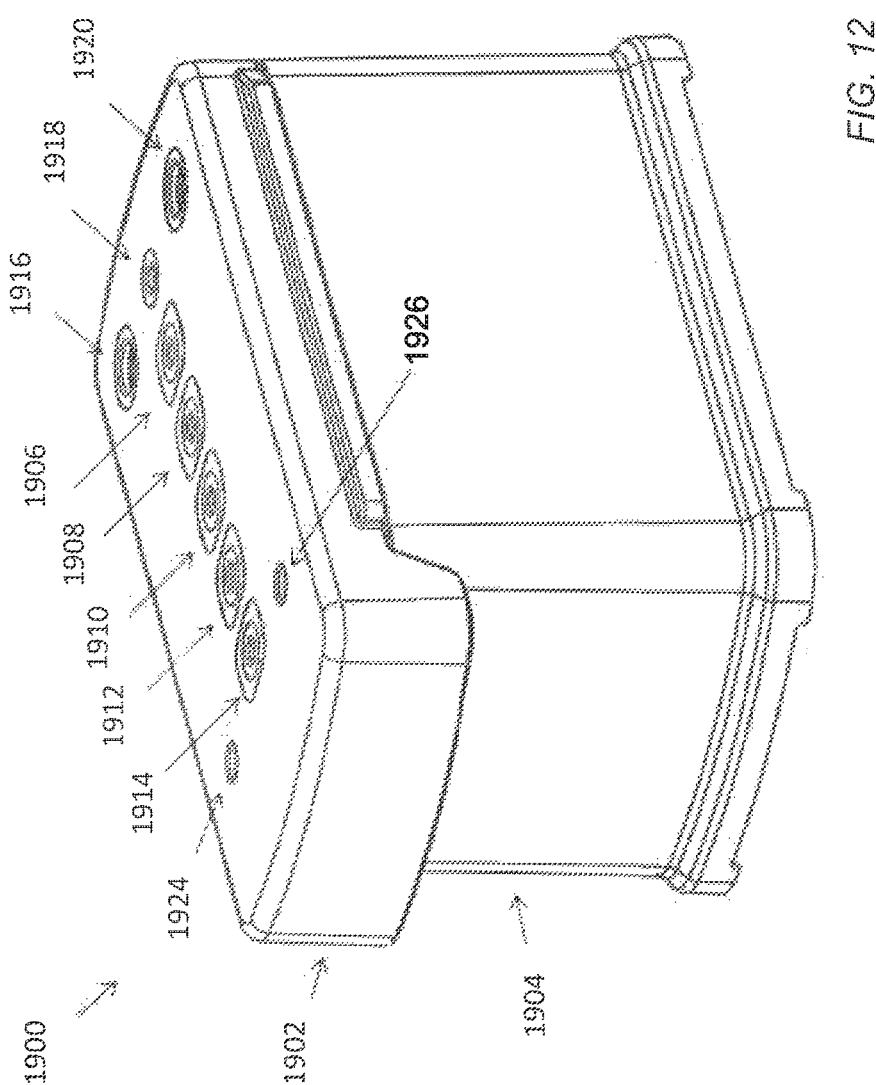
FIG. 12, FIG. 13, FIG. 14, FIG. 15, and FIG. 16 include illustrations of an exemplary cartridge for enclosing one or more enclosures.

In a particular example illustrated in FIG. 12, a cartridge or case 1900 includes a lid 1902 and a body 1904. The lid 1902 can receive the fluid ports (1906, 1908, 1910, 1912, or 1914) of containers inserted into flexible enclosures. The container can include different reagents. For example, each container can include a nucleotide or can include a pH-adjusting reagent. The lid 1902 can also include a port 1916 for providing pressurized gas or relieving the pressure, controlling the pressure outside of each of the enclosures and thereby controlling pressure within the enclosure. The walls of the base 1904 and the lid 1902 can be configured to permit pressurizing a cavity within the cartridge 1900, for example, with pressurized gas or air. In an example, the cartridge 1900 can be labeled with a bar code or radio frequency identification (RFID) tag.

Figure 13:
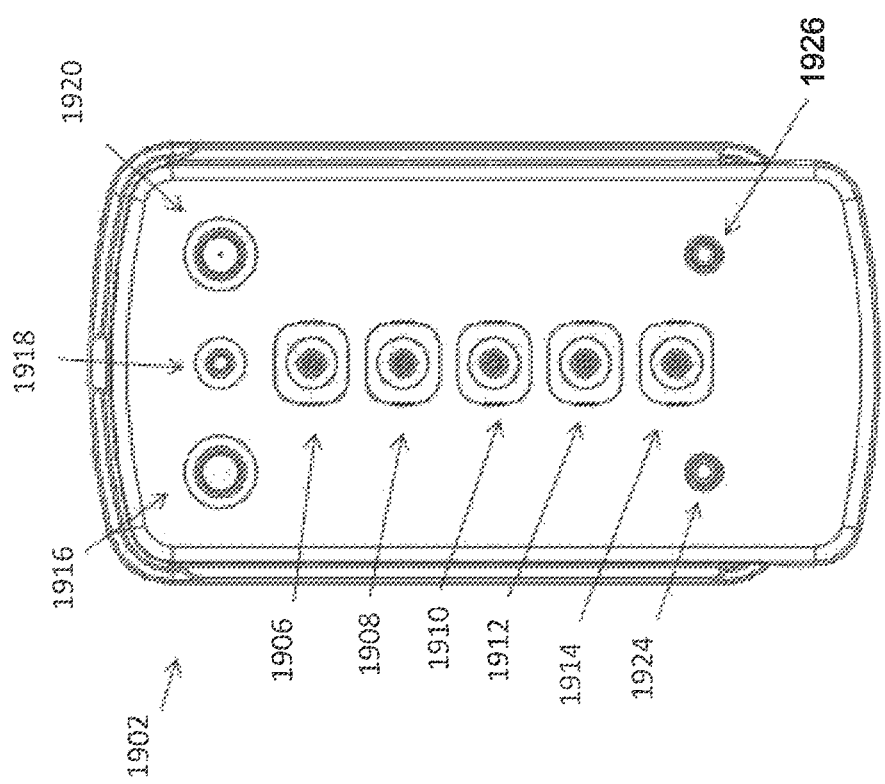

As illustrated in FIG. 12 and FIG. 13, the lid 1902 can include access ports 1918 and 1920 for applying gas or air through a scrubber cartridge. In particular, system can utilize external air, applying the external air through the port 1918 and receiving a cleaned gas or air through the port 1920. In particular, the scrubber cartridge can include absorbent materials for capturing carbon dioxide or water. Carbon dioxide can be removed from air to prevent acidification of liquid components when carbon dioxide diffuses into the enclosures or when the air is used in other parts of the system.

In a further example, the lid 1902 can also include alignment features 1924 or 1926. Such alignment features can be used to align access to the ports (1906, 1908, 1910, 1912, 1914, 1916, 1918, or 1920) with a manifold to limit damage to the manifold or provide for adequate engagement between the manifold and the case 1900.

Figure 14:
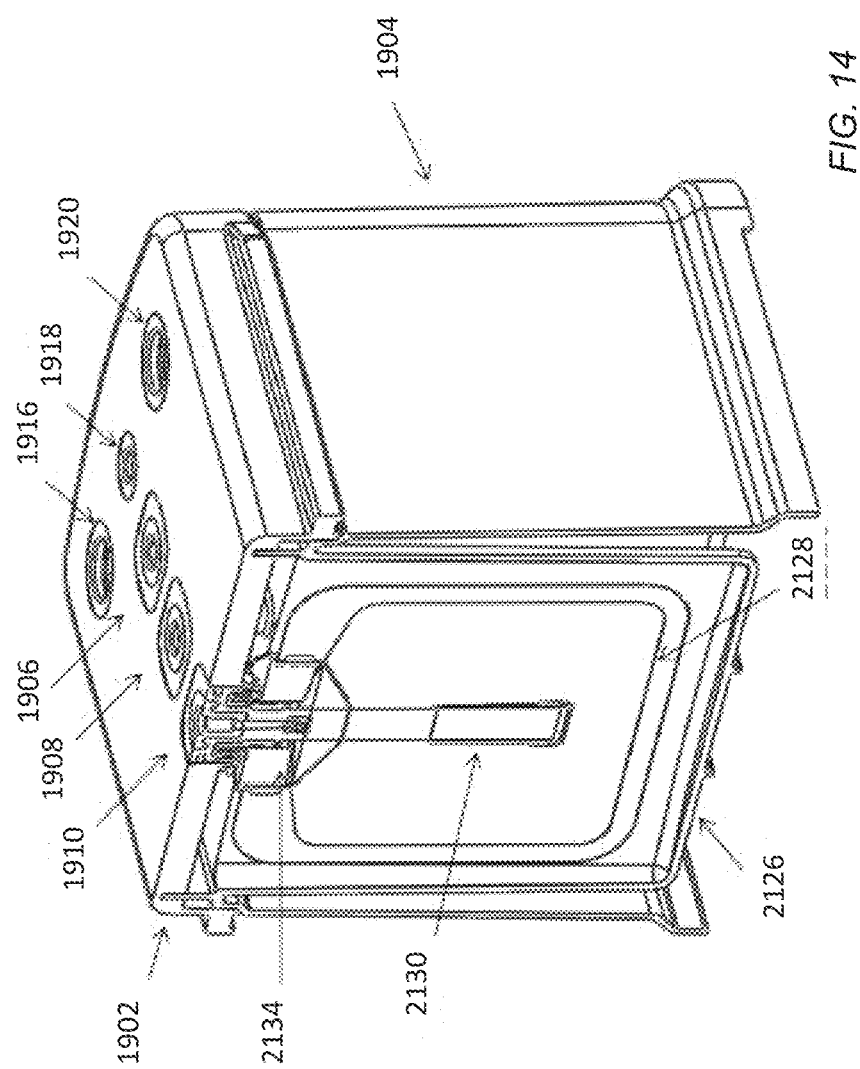
Figure 15:
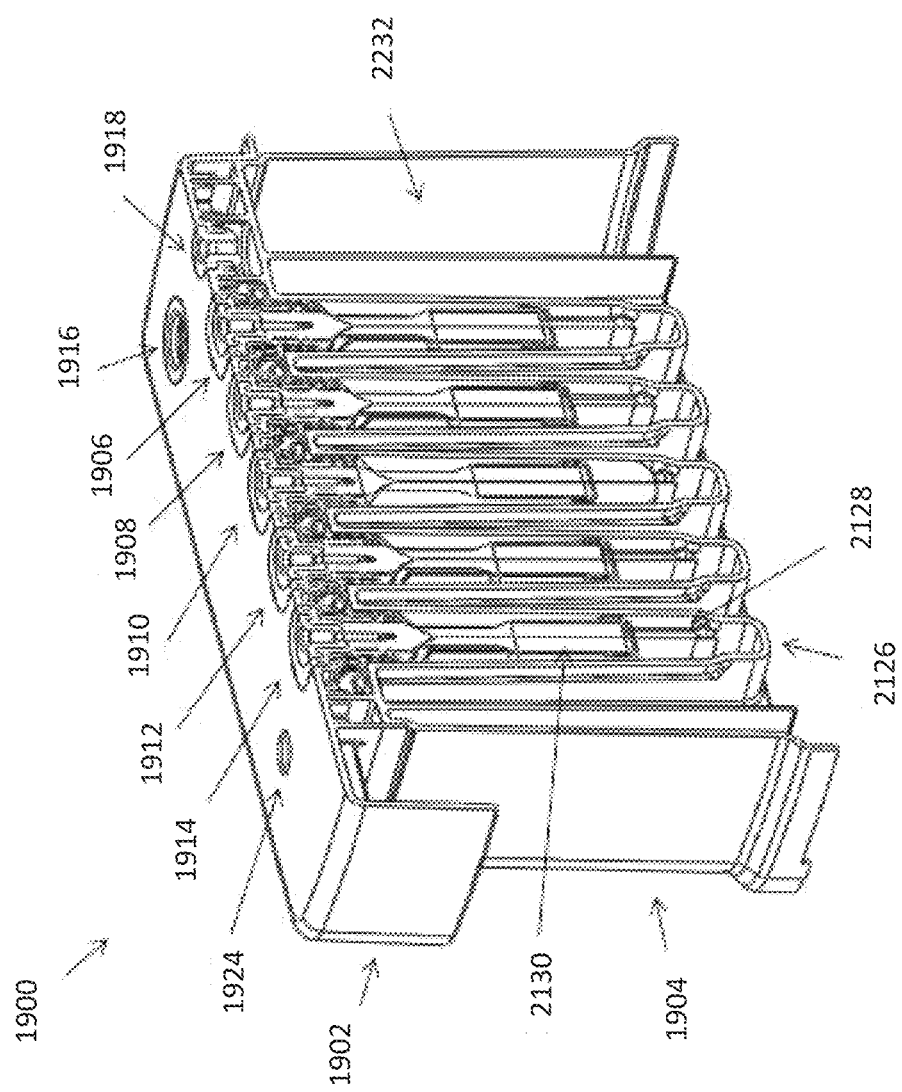
Figure 16:
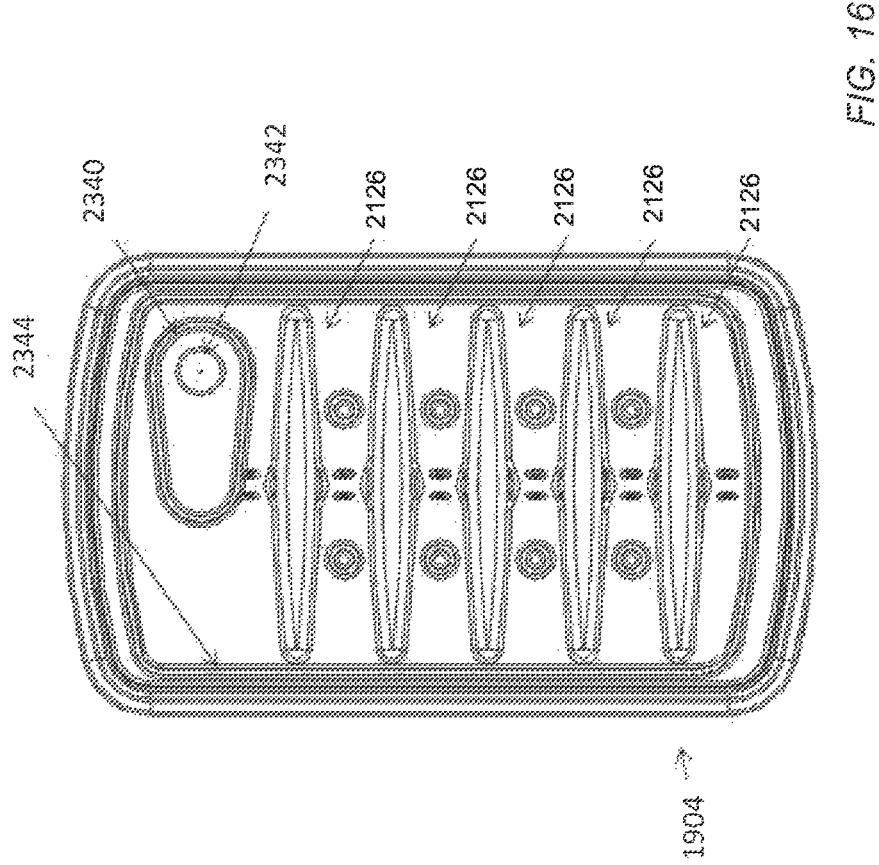

As illustrated in FIG. 14, FIG. 15, and FIG. 16, the body 1904 can define individual cavities 2126 into which each enclosure 2128 is placed and the nucleotide container 2130 is inserted. In an example, each enclosure 2128 is disposed within individual cavities 2126 and each container 2130 is applied through the lid 1902, engaging the lid 1902 at the fluid port of the container 2130. A fitting 2134 of the enclosures 2128 can engage the lid 1902.

The lid 1902 can define a headspace that provides communication between the pressurized gas input port 1916 and each of the cavities 2126. Alternatively, the cavity can be an open cavity absent individualized cavities 2126 and provide a single cavity to which pressurized gas can be applied to apply pressure to the enclosures 2128. As illustrated in FIG. 15, the body 1904 can include a chamber 2232 to receive a scrubber cartridge, for example, for removing carbon dioxide from the air.

In a top view, as illustrated in FIG. 16, the body 1904 includes individualized cavities 2126. In addition, the body can include a seal structure 2340 to isolate the scrubber cartridge input and output from the pressure of the rest of the body 1904. In addition, an internal seal 2342 can be utilized to isolate the input pressure of air entering the scrubber cartridge from the output pressure of air leaving scrubber cartridge. Further, the body 1904 can include a seal structure 2344 to engage an opposing seal structure on the lid 1902 to provide an isolated interior space including the cavities that can be pressurized or depressurized.

The containers can include nucleotide reagents or other reagents. In particular, individual containers within the cartridge system can include one of four nucleotides. The system can also include a container within an enclosure that includes pH-adjusting reagents. In a particular example, the cartridge includes containers and enclosures incorporating each of the four nucleotides (A, G, C, or T) and optionally, a pH-adjusting reagent container. In an example, the reagents are in dried form. For example, lyophilized nucleotides can be stored within the container. In another example, a reagent solution can be absorbed within a porous metallic, ceramic, or polymeric sponge-like material or frit. In a further example, the reagent solution can be frozen either within a container or within the porous sponge-like material into which the reagent solution is absorbed.

The enclosures described herein can be applied to prepare a reagent solution. Assembly of the enclosure includes inserting a container into the enclosure and sealing the container within the enclosure with a fluid port. One or more enclosures can be further secured into a volume of a case, where the case includes a gas port for providing external gas pressure to the secured enclosures. The enclosures can be inserted into a case as a final assembly step or at a point just prior to mixing that provides flexibility of in the selection of reagents.

Alternatively, the enclosure can be secured to the lid prior to inserting the containers including reagent. The reagent containers can be inserted through the lid and the fluid port of the containers can engage the lid. The lid can be secured to the base following securing the enclosures to the lid or following inserting the containers through the lid into the enclosures.

The pressurization and depressurization of the fluid within the enclosures are controlled by increasing and decreasing the gas pressure of the volume of the case via the gas port.

A method for preparing a reagent solution includes filling an enclosure, such as any of the enclosures described herein including a container and a reagent, with a predetermined amount of fluid through a fluid port of the enclosure. The fluid within the enclosure is then pressurized such that fluid flows into the internal cavity of the container through a passage of the container. The fluid can be pressurized directly through a port. In another example, the fluid can be pressurized by applying external pressure to the enclosure, for example, using gas or other fluidic pressure. The pressurization compresses the compressible volume or member within the internal cavity of the container while the fluid fills a portion of the volume of the internal cavity.

For example, the fluid flows into the internal cavity of the container and compresses the compressible volume or member until the pressure within the internal cavity and exerted on the compressible volume or member is approximately equal to a pressure within the enclosure and external to the container.

After reaching a predetermined pressure, the fluid within the enclosure is depressurized. The compressible volume or member decompresses so as to expand and eject the fluid and reagent from the internal cavity into the enclosure outside of the container. The mixture of reagent and fluid ejected from the passage creates eddy currents and turbulence within the bag enclosure sufficient to mix the reagent with fluid. Upon depressurization, a pressure within the internal cavity as imposed by the compressible volume or member is greater than a pressure within the enclosure and external to the container. The fluid and the reagent eject from the internal cavity through the passage until the pressure within the internal cavity is approximately equal to a pressure within the enclosure and external to the container to provide a well-mixed reagent solution.

Pressurization can be performed by increasing a gas pressure external to a flexible enclosure. In one implementation, the enclosure can be disposed within a case. Pressure within the enclosure can be controlled by increasing/decreasing a gas pressure within the case and external to the enclosure. Proper mixing of the reagent and fluid can be accomplished through repeated cycles of pressurization and depressurization. After mixing is completed, the fluid and the reagent are released through the fluid port of the enclosure.

Figure 17:
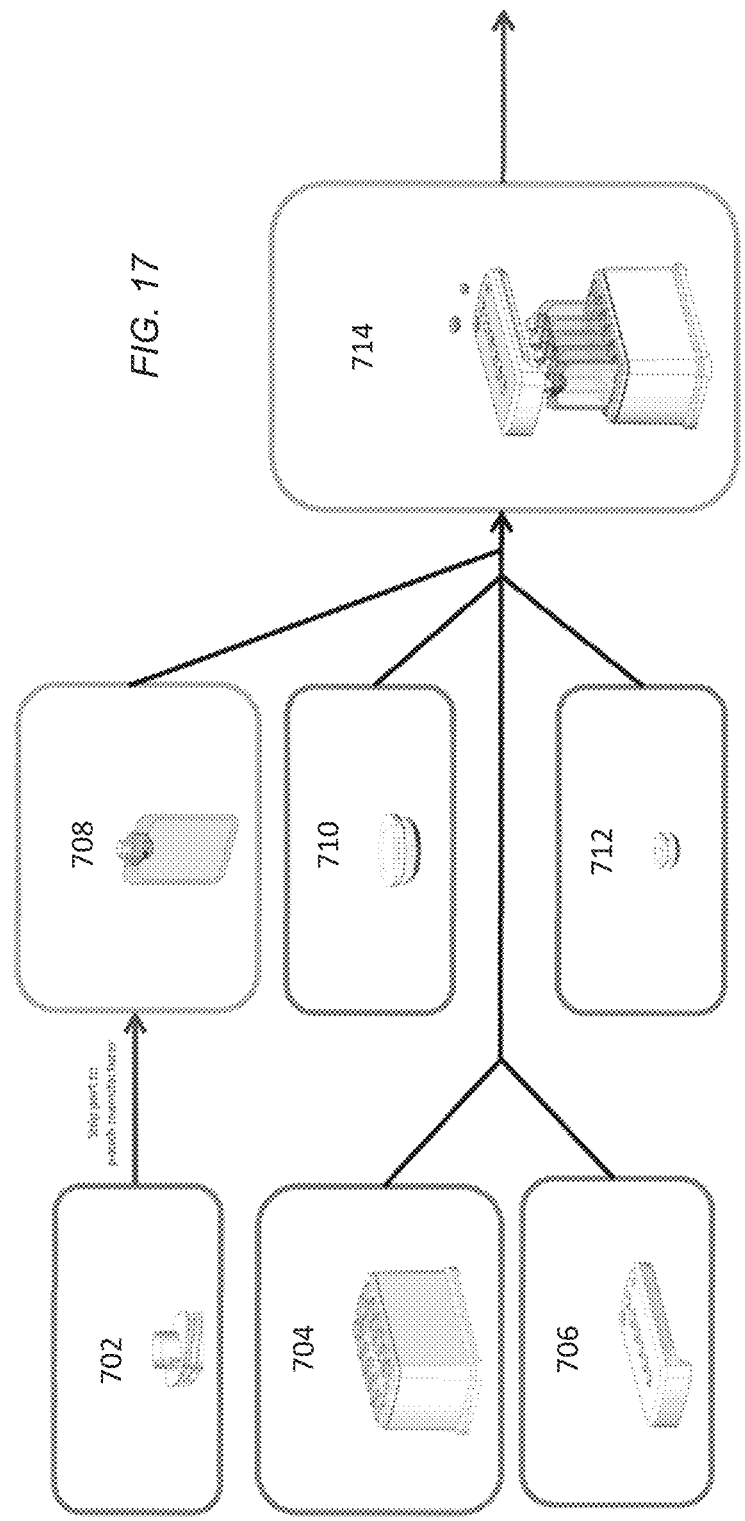
FIG. 17 and FIG. 18 illustrate a schematic of an example method.
Figure 18:
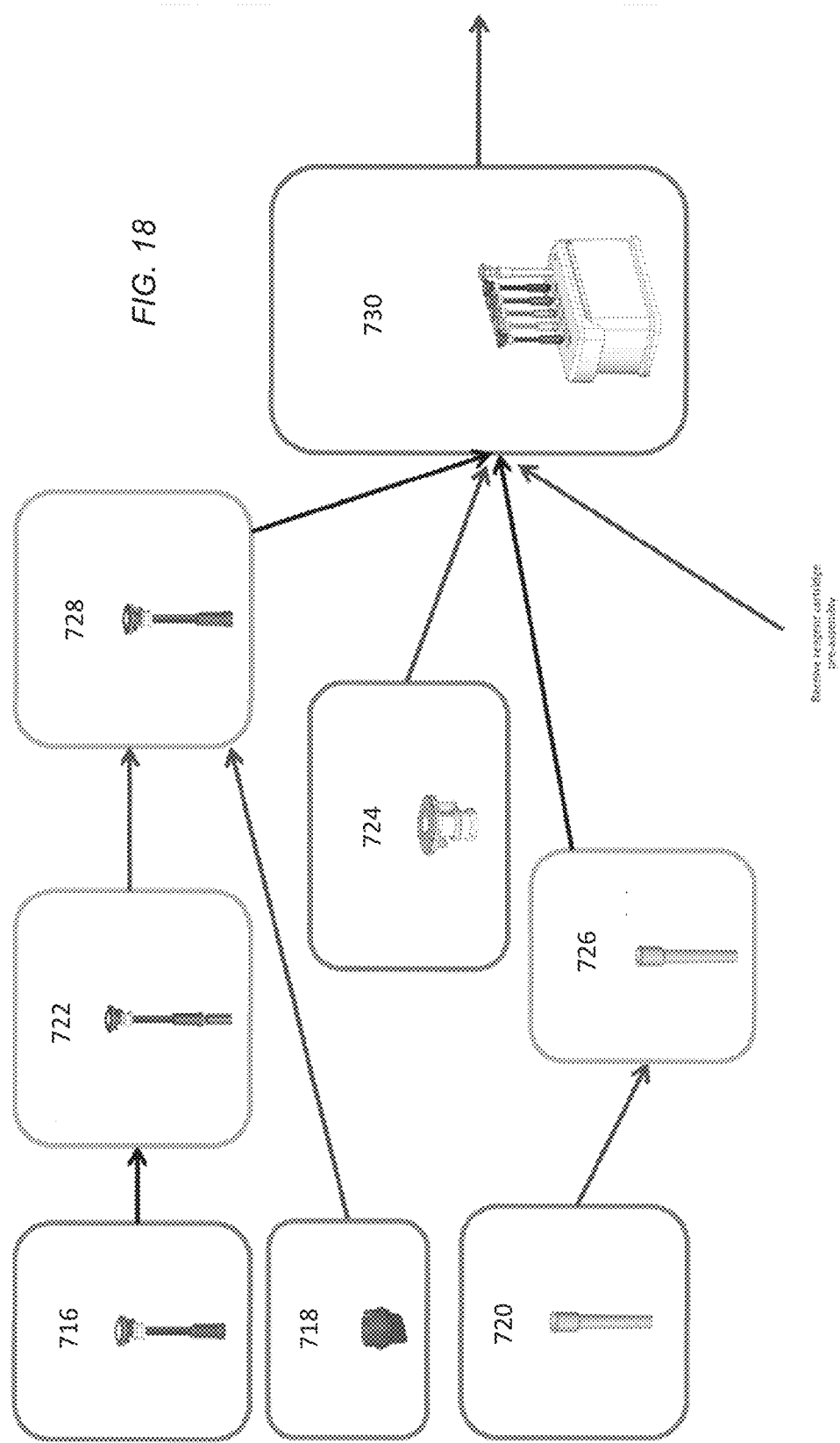

FIG. 17 and FIG. 18 illustrated an exemplary method for assembling a reagent cartridge. For example, a fitting 702 can be secured to a bag enclosure form an enclosure 708. A plurality of enclosures 708 can be coupled to a lid 706 of a cartridge and inserted into a cartridge base 704, as illustrated 714, when the cartridge lid 706 is secured to the cartridge base 704. A port gasket 710 can be secured to the cartridge lid to permit connection of the compressed air system to the cartridge. In a further example, a port gasket 712 can be secured to the cartridge lid 706 to permit access to a $CO_2$ scrubber.

Turning to FIG. 18, reagent containers can be formed by inserting an optional compressible member into a first portion 716 of the reagent container, as illustrated at 722. A second part 718 can be secured to the first part 716 to form the reagent container 728. Optionally, the reagent is applied to the second part 718. Alternatively, the reagent is inserted into the first portion at 722.

A scrubber container 720 can be filled with scrubbing reagent to remove $CO_2$, for example, as illustrated at 726. A plurality of reagents containers 728 and the scrubber container 720 can be inserted into the reagent cartridge through the lid, as illustrated 730. The ends of the reagent cartridge containers 728 are supplied through the cartridge lid and into the interior of the reagent enclosures. The scrubber container 720 is inserted through the lid and into an isolated compartment of the cartridge that permits air to flow in and out without influencing the pressure in the remaining cavity of the cartridge. Fluid port gaskets 724 are secured over the reagent containers and optionally the scrubber container to provide for fluid tight access to the reagent containers or scrubber container when secured within a manifold and instrument.

Figure 19:
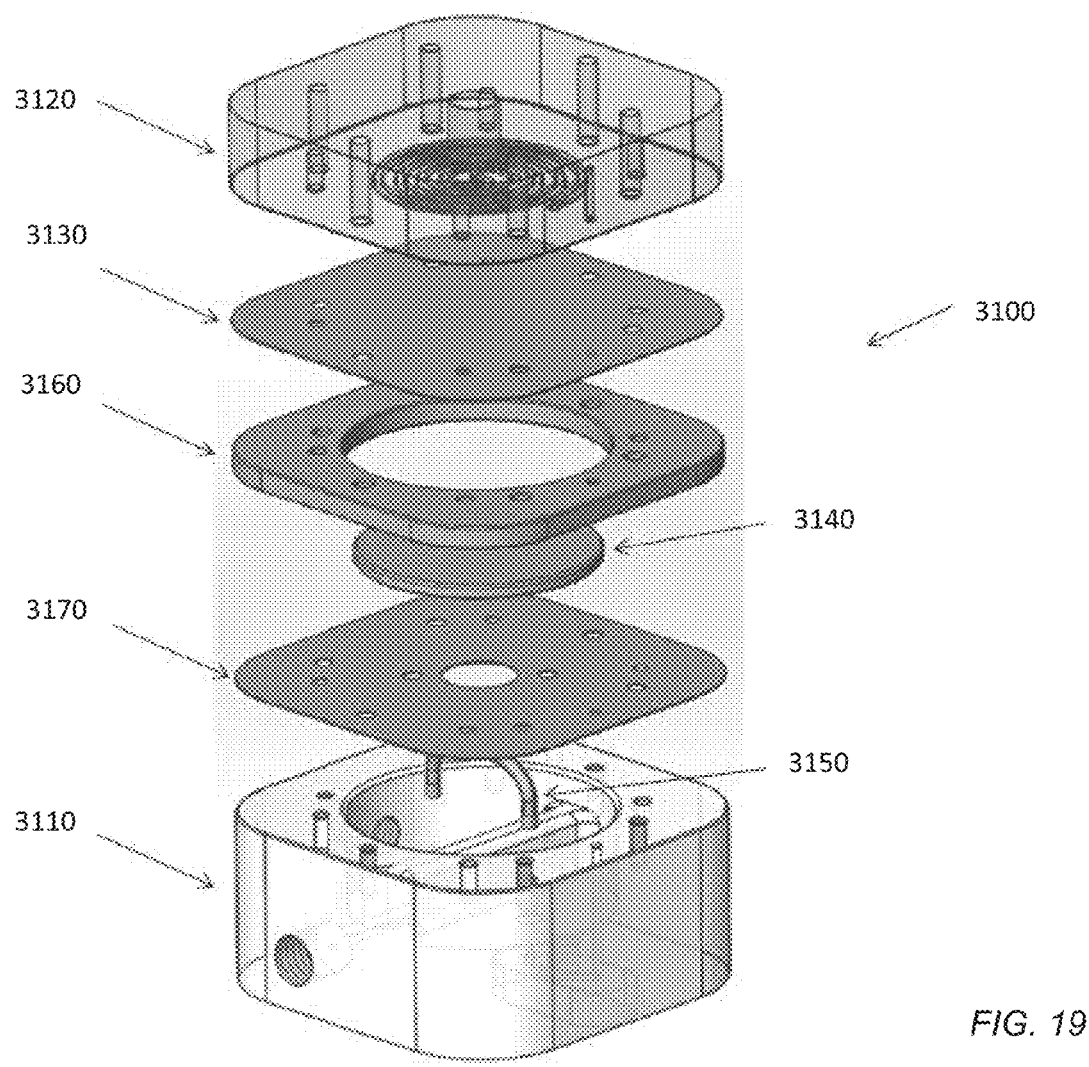
FIG. 19 is an exploded schematic view describing an example valve.

FIG. 19 provides an exploded schematic view of an example pinch valve regulator 3100. The valve 3100 includes a housing base 3110 and a housing cover 3120 disposed above the base 3110. A diaphragm 3130 is disposed between the housing base 3110 and the housing cover 3120. A pinch plate 3140 is disposed between the diaphragm 3130 and the base 3110. In operation, the pinch plate 3140 moves relative to the housing base 3110 to pinch a pinch tube 3150 against a pinch structure (as illustrated more clearly in FIGS. 20, 21 and 22) to restrict fluid flow through the pinch tube 3150. One or more gaskets 3160, 3170 can be disposed between the housing base 3110 and housing cover 3120 to prevent fluid leakage and to ensure smooth valve operation.

Figure 20:
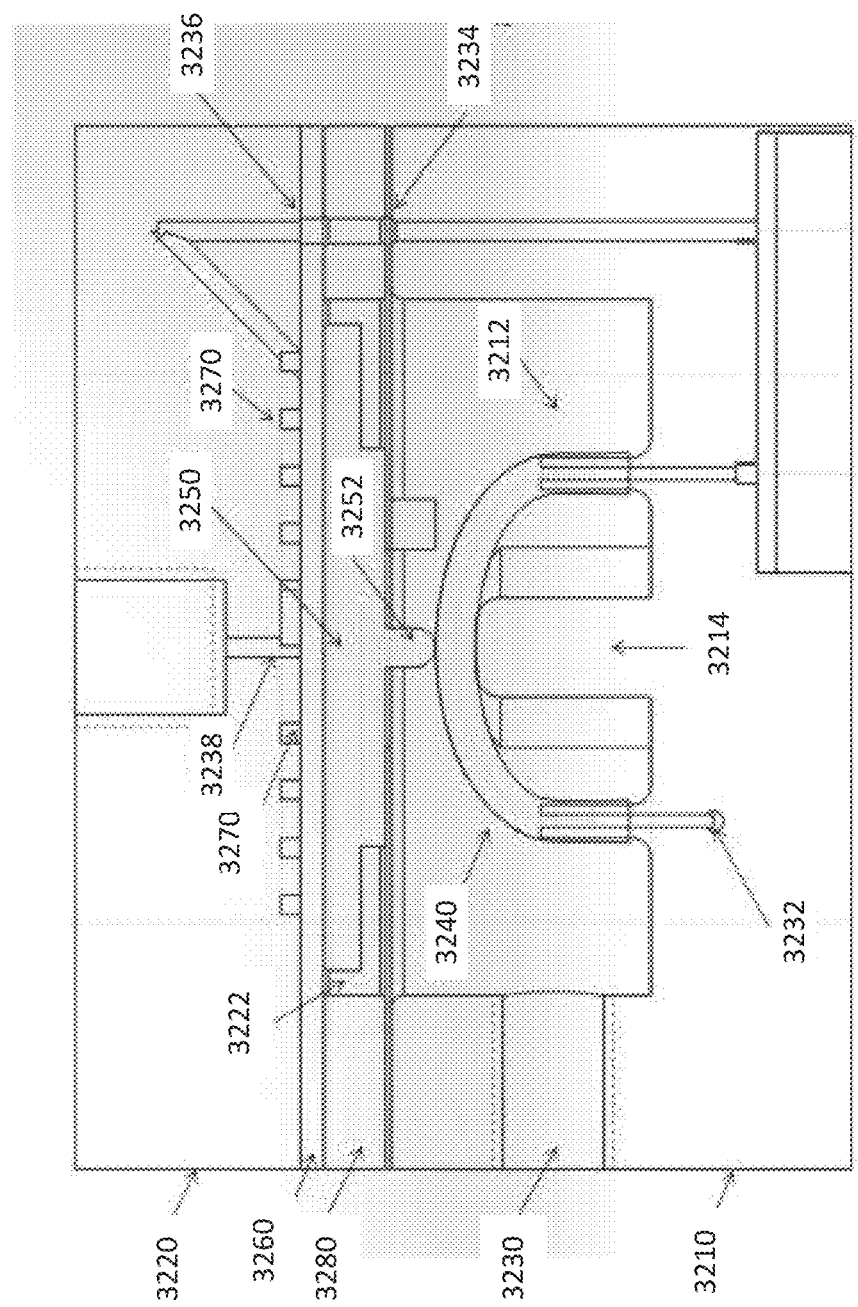
FIG. 20 is a cross-sectional schematic view describing an example valve.

FIG. 20 provides a cross-sectional schematic view of an example pinch valve regulator. A valve 3200 includes a housing base 3210 and a housing cover 3220 disposed over of the base 3210. The housing base 3210 includes a lower cavity 3212 and a pinch structure 3214 protruding within the lower cavity 3212. The housing base 3210 includes a gas inlet 3230, providing external access to the lower cavity 3212. A base fluid inlet 3232 provides an external access path that is connected to one end of a pinch tube 3240 within the lower cavity 3212. The other end of a pinch tube 3240 is connected to a base fluid outlet 3234. Accordingly, the pinch tube 3240 provides fluidic communication between the base fluid inlet 3232 and the base fluid outlet 3234. The pinch tube 3240 extends between the pinch structure 3214 and a pinch point 3252 of a pinch plate 3250.

In an example, the pinch structure 3214 includes a rectangular prism extending into the lower cavity 3212. As illustrated, the rectangular prism as a rounded top. In another example, the rectangular prism can have a flat top. Alternatively, the prism can have a pointed structure, such as a triangular prims. In general, the pinch structure 3214 forms a counter structure to which the pinch point 3252 can secure and punch the pinch tube 3240.

The base fluid outlet 3234 is in turn connected to and provides fluidic communication with a cover fluid inlet 3236 between the upper cavity and the lower cavity to provide a fluid path through the housing base 3210 and the housing cover 3220. The cover fluid inlet 3236 is in fluidic communication with a cover fluid outlet 3238 via a fluid path 3270. The cover fluid outlet 3238 provides external access to the fluid path 3270 from the housing cover 3220. A diaphragm 3260 is disposed between the housing base 3210 and the housing cover 3220 to fluidically separate the lower cavity 3212 from an upper cavity 3222 defined between the cover 3220 and the diaphragm 3260.

The housing cover 3220 defines an upper cavity 3222 where the fluid path 3270 is disposed. Optionally a gasket 3280 can define part of the lower cavity 3212 or part of the upper cavity 3222. The pinch plate 3250 can be disposed within the cavity region defined by the housing cover 3220 or the gasket 3280. The base fluid outlet 3234 and the cover fluid inlet 3236 are in fluidic communication through the gasket 3280 and diaphragm 3260. Alternatively, the base fluid outlet 3234 and the cover fluid inlet 3236 can be fluidically connected external to the housing base 3210 or the housing cover 3220. The diaphragm 3260 provides separation between the lower cavity 3212 and the upper cavity 3222. A pinch plate 3250 is disposed within the cavities 3212, 3222 defined within the housing cover 3220 and the housing base 3210. The pinch plate 3250 includes a pinch point 3252 that is disposed opposite the pinch structure 3214. The pinch point 3252 is illustrated with a rounded tip. Alternatively, the pinch point 3252 can have a sharp tip. The pinch plate 3250 moves relative to the housing base 3210 to pinch the pinch tube 3240 to restrict fluid flow through the pinch tube 3240 based on fluid pressure within the fluid path 3270 and gas pressure within the lower cavity 3212.

Figure 21:
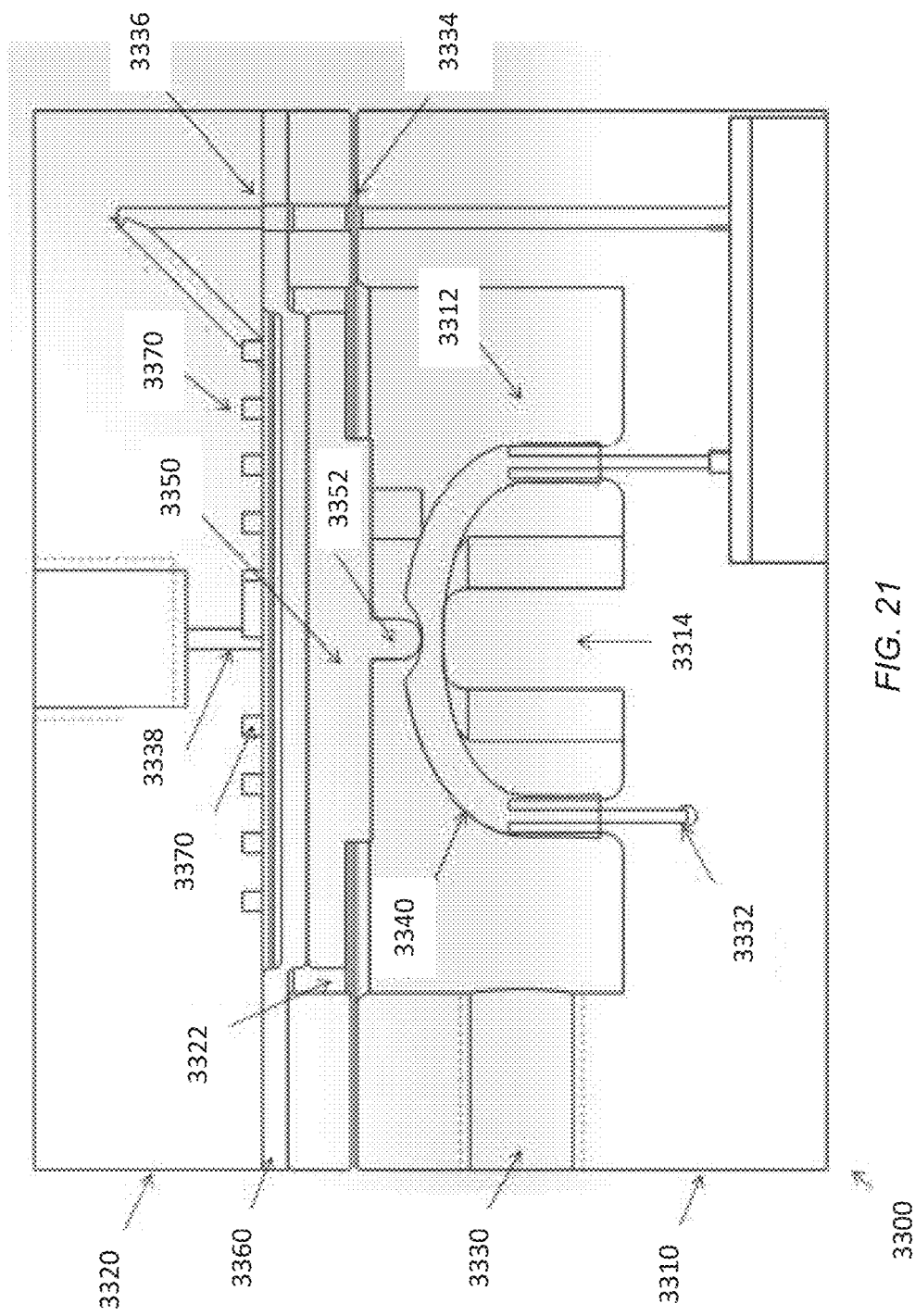
FIG. 21 is a cross-sectional schematic view describing an example valve.
Figure 22:
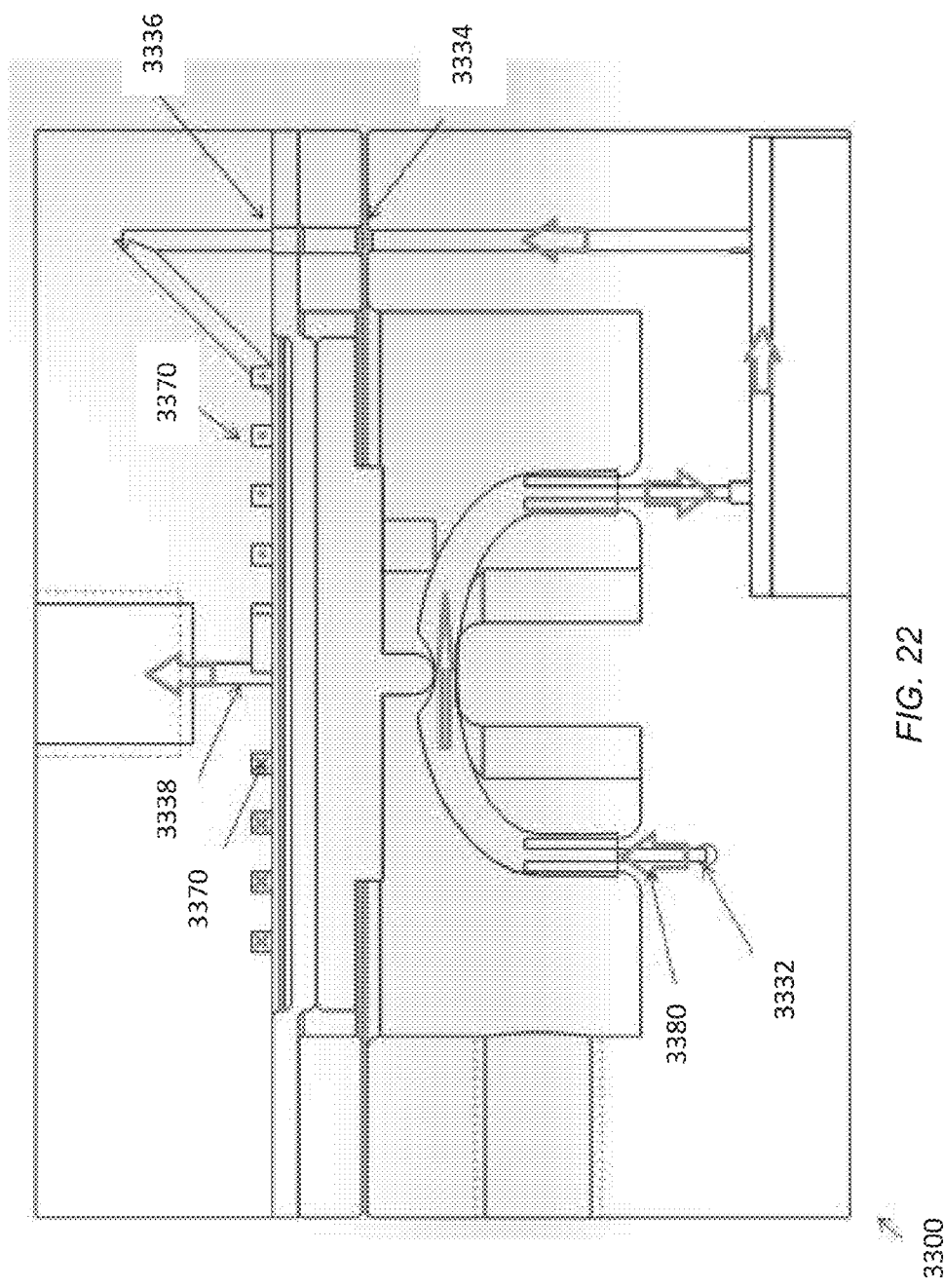
FIG. 22 is a cross-sectional schematic view describing an example valve.

The valves described herein operate to regulate fluid flow as a function of gas pressure within the lower cavity. FIG. 20 illustrates a valve structure prior to applying fluid into the valve 3200 and FIGS. 21-22 illustrate an equilibrium state of a valve where fluid flows through valve 3300 at a flow rate based on the input gas pressure. An implementation of the pinch valve in operation will be described below with reference to FIG. 20. FIG. 21 and FIG. 22.

Gas pressure is applied to a gas inlet 3230, 3330 of the valve to pressurize the lower cavity 3212, 3312 at an input/reference gas pressure. The pressurized lower cavity applies an upward force against the pinch plate 3250, 3350 and diaphragm 3260, 3360 towards the housing cover 3220, 3320. Fluid is applied to the base fluid inlet 3332 and flows sequentially through pinch tube 3340, base fluid outlet 3334, cover fluid inlet 3336, fluid path 3370, cover fluid outlet 3338, and then out of the valve. The fluid flowing through the housing cover 3320 applies a downward force against the diaphragm 3360 and pinch plate 3350 towards the housing base 3310. As the fluid pressure in the fluid path 3370 increases relative to the gas pressure in the lower cavity 3312, the diaphragm 3360 moves toward the housing base 3310 and applies downward force against the pinch plate 3350. In particular, the diaphragm 3360 is to motivate the pinch point 3352 relative to the pinch structure 3314 in response to a difference between a fluid pressure in the upper cavity 3322 and a gas pressure in the lower cavity 3312. For instance, "the diaphragm 3360" is to motivate the pinch point 3352 towards the pinch structure 3314 in response to an increase in the fluid pressure within the upper cavity 3322 relative to the gas pressure in the lower cavity 3312 to restrict fluid flow in the pinch tube 3340.

As the pinch plate 3350 moves toward the housing base 3310, the pinch point 3352 applies a downward force onto pinch tube 3340 so as to pinch the tube 3340 against the pinch structure 3314 and restrict fluid flow or cause a pressure drop across the punch tube 3340 and in the upper cavity 3322 until the input gas pressure counteracts the fluid pressure in the upper cavity 3322 to thereafter provide a constant fluid flow rate from the valve 3300. FIG. 22 illustrates a valve 3300 with directional arrows 3380 indicating the fluid flow path through the valve 3300.

The pinch actuation force of the diaphragm driven pinch valve is such that the output fluid pressure is regulated by the input gas pressure. By setting the pressure in the lower gas cavity 3312 to a known value, fluid flow and pressure exiting the "housing cover 3320" is controlled. In this manner, the valve self-regulates to reach equilibrium and can provide a desired constant fluid flow. In summary, the output fluid pressure at the cover fluid outlet follows the input gas pressure at the gas inlet and can be independent of the fluid pressure at the base fluid inlet.

Figure 23:
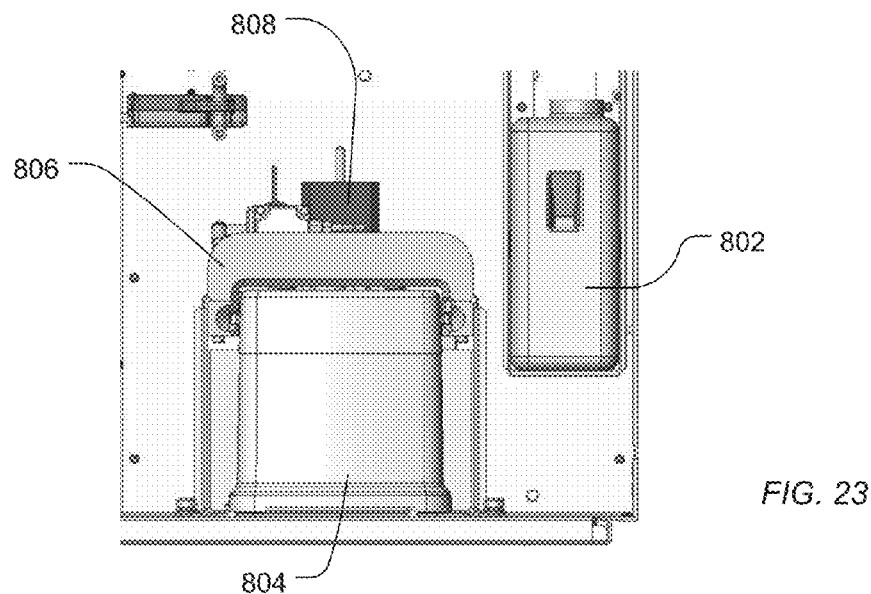
FIG. 23 and FIG. 24 include illustrations of an example manifold and cartridge.
Figure 24:
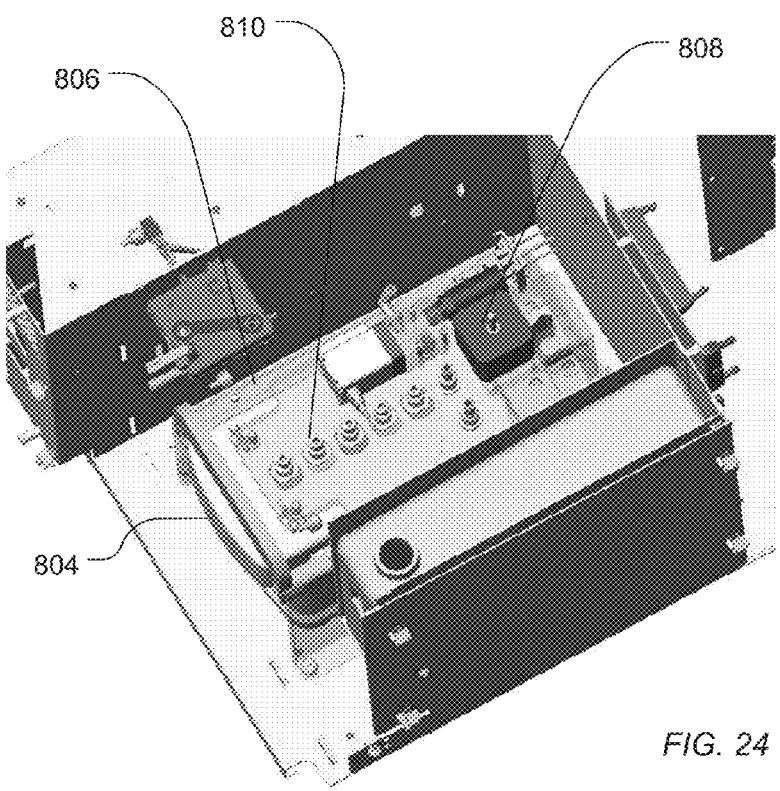

FIG. 23 and FIG. 24 include illustrations of an exemplary sequencing system that includes a manifold 806 to receive a cartridge 804. The manifold may be driven up and down using an actuator 808. Optionally, a waste vessel 802 can be positioned within the instrument and fluidically connected to the cartridge 804, for example, as illustrated in the schematic of FIG. 2.

Figure 2:
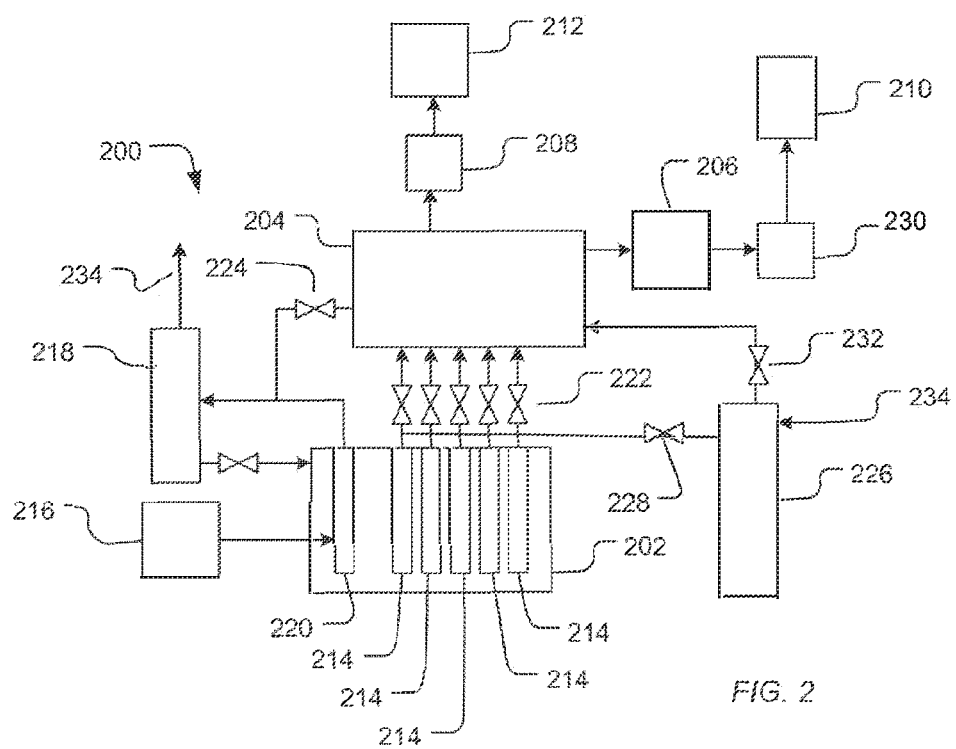
FIG. 2 includes a schematic of an example sequencing instrument.

As illustrated in FIG. 24, a plurality of fluid ports 810 can be connected to tubing and a fluidic circuit, such as the fluidics schematic illustrated in FIG. 2. The cartridge 804 can optionally include an RFID tag readable by the instrument. Connection of the manifold 806 to the cartridge 804 can be prevented or permitted based on the reading of the RFID tag.

FIG. 25 diagrammatically illustrates another embodiment of the fluidics circuit of the invention which accommodates five input reagents in a planar circuit structure. FIG. 25 is a top view of a transparent body or housing 4300 containing fluidic circuit 4302. A housing can be constructed from a variety of materials, including metals, glass, ceramics, plastics, or the like. Transparent materials include polycarbonate, polymethyl methacrylate, and the like. Inlets (or input ports) are connected by a passage to their respective connector slots (e.g. 4370) located on the bottom side of housing from which reagents enter fluidic circuit 4302. Inlets are in fluid communication with passages (e.g., 4353) which, in turn, are connected to curvilinear passages. Each curvilinear passage consists of two legs, identified for curvilinear passage at a "T" junction 4356. One leg is an inner leg which connects its respective inlet to node (or multi-use central port) 4301 and the other leg is an outer leg which connects its respective inlet to waste passage (or ring) 4340. As mentioned above, the cross-sectional areas and lengths of the inner and outer legs of the curvilinear passages may be selected to achieve the desired balance of flows at the "T" junctions and at node 4301. Through passage, waste passage (or channel) 4340 is in fluid communication with waste port 4345 which connects to a waste reservoir (not shown) by connector slot on the bottom side of body. Node 4301 is in fluid communication with port 4363 by passage 4361 which in this embodiment is external to body 4300 and is illustrated by a dashed line. In other embodiments, passage 4361 may be formed in body so that connector slots for node 4301 and port 4363 are not required. Port is connected by passage 4363 to wash solution inlet, where a "T" junction is formed, and to connector slot which, in turn, provides a conduit to a flow cell, reaction chamber, or the like. FIG. 25 illustrates a mode of using the fluidics circuit to distribute fluids to a flow cell. The modes of operation are implemented by valves 4350 associated with each of the input reagents and with the wash solution. In a first mode of operation (selected reagent valve open, all other reagent valves closed, wash solution valve closed) a selected reagent is delivered to a flow cell; in a second mode of operation (selected reagent valve open, all other reagent valves closed, wash solution valve open) the fluidic circuit is primed to deliver a selected reagent; and in a third mode of operation (all reagent valves closed wash solution valve open) (not shown), all passages in the fluidics circuit are washed. As mentioned above, associated with each inlet is a valve 4350 which can be opened to allow fluid to enter fluidic circuit 4302 through its respective inlet (as shown for valve (4352)), or closed to prevent fluid from entering circuit 4302 (as shown with all valves, except for 4352). In each case, when an inlet's valve is open and the others are closed (including the wash solution valve) as shown for inlet 4370 in the FIG. 25, fluid flows through passage 4354 to "T" junction 4356 where it is split into two flows, one of which is directed to waste passage 4340 and then the waste port 4345, and another of which is directed to node 4301. From node 4301 this second flow again splits into multiple flows, one of which exits node 4301 through passage 4361 and then to passage 4363 and to a flow cell and the other flows to each of the passages connecting node 4301 to the other inlets, and then to waste passage 4340 and waste port 4345. The latter flows pass the other inlets carrying any material diffusing or leaking therefrom and directing it to waste port 4345. A sequence of different reagents may be directed to a flow cell by opening the valve of a selected reagent and simultaneously closing the valves of all of the non-selected reagents and the wash solution. In one embodiment, such sequence may be implemented by a sequence of operating modes of the fluidics circuit such as: wash, prime reagent x1, deliver reagent x1, wash, prime reagent x2, deliver reagent x2, wash, and so on. For the reagent priming mode, as in the reagent delivery mode, all reagent inlet valves are closed, except for the valve corresponding to the selected reagent. Unlike the reagent delivery mode, however, the wash solution valve is open and the relative pressure of the selected reagent flow and the wash solution flow is selected so that wash solution flows through passage 4361 and into node 4301 where it then exits through all the passages leading to waste passage 4340, except for the passage leading to the selected reagent inlet.

Figure 26:
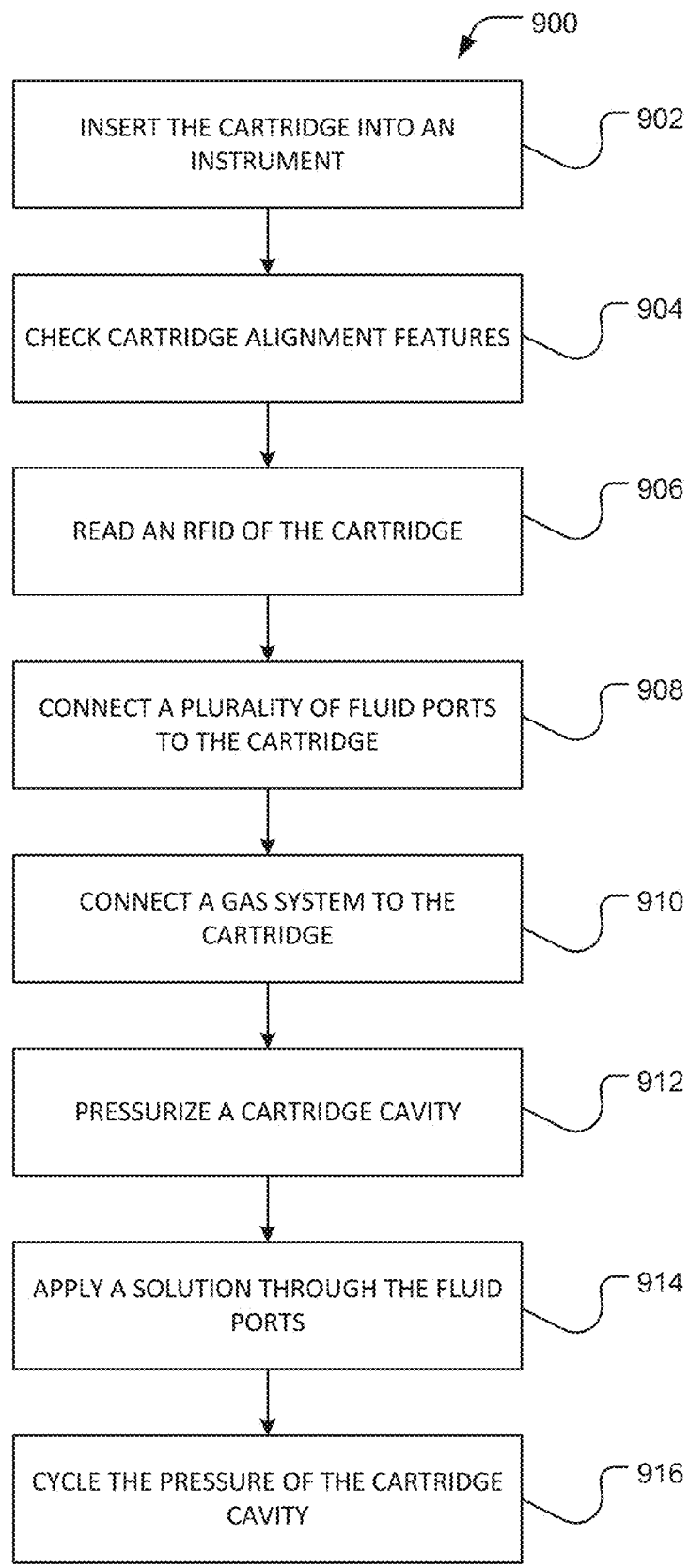
FIG. 26 includes a flow diagram of an example method for preparing a reagent solution.

As illustrated in FIG. 26, a method 900 for preparing a reagent solution within a cartridge includes inserting the cartridge into an instrument, as illustrated 902. For example, the cartridge can be inserted under a manifold, similar to the embodiments illustrated in FIG. 23 or FIG. 24, or the instrument illustrated in FIG. 1.

Optionally, the system can check the cartridge alignment features, as illustrated 904. For example, the cartridge can include structures that indicate proper positioning of the cartridge within the instrument. As further illustrated at 906, that the cartridge can optionally include a radio frequency identifier tag (RFID tag) that can be read by the instrument. Based on the test of the cartridge alignment features or the reading of the RFID tag of the cartridge, the instrument can selectively engage the cartridge using a manifold.

For example, the instrument can connect a plurality of fluid ports secured to the manifold to the cartridge, providing fluidic connectivity with the rest of the instrument, as illustrated 908. The instrument can further connect a gas system, such as a compressed air system, to the cartridge, as illustrated 910. In an example, the connections to the gas system are incorporated within the manifold that connects the fluid ports to the reagent cartridges. In particular, the system can be connected to the scrubber inlet and outlet and optionally to the cavity defining space between the reagent enclosures.

As illustrated at 912, the cartridge cavity can be pressurized. The enclosures or reagent enclosures can evacuate as a result of the pressurizing of the cartridge cavity. Following evacuation of the enclosures, the cartridge cavity can further be depressurized.

A solution (e.g., a buffered solution) can be applied through the fluid ports, as illustrated at 914. In particular, the solution can be universally applied to each of the reagent enclosures. Following application of the solution, the pressure within the cartridge cavity and can then be cycled "as illustrated at 916". Such cycling can cause mixing of reagents within the enclosures, for example utilizing the mechanisms described above in relation to FIGS. 4-16.

Figure 27:
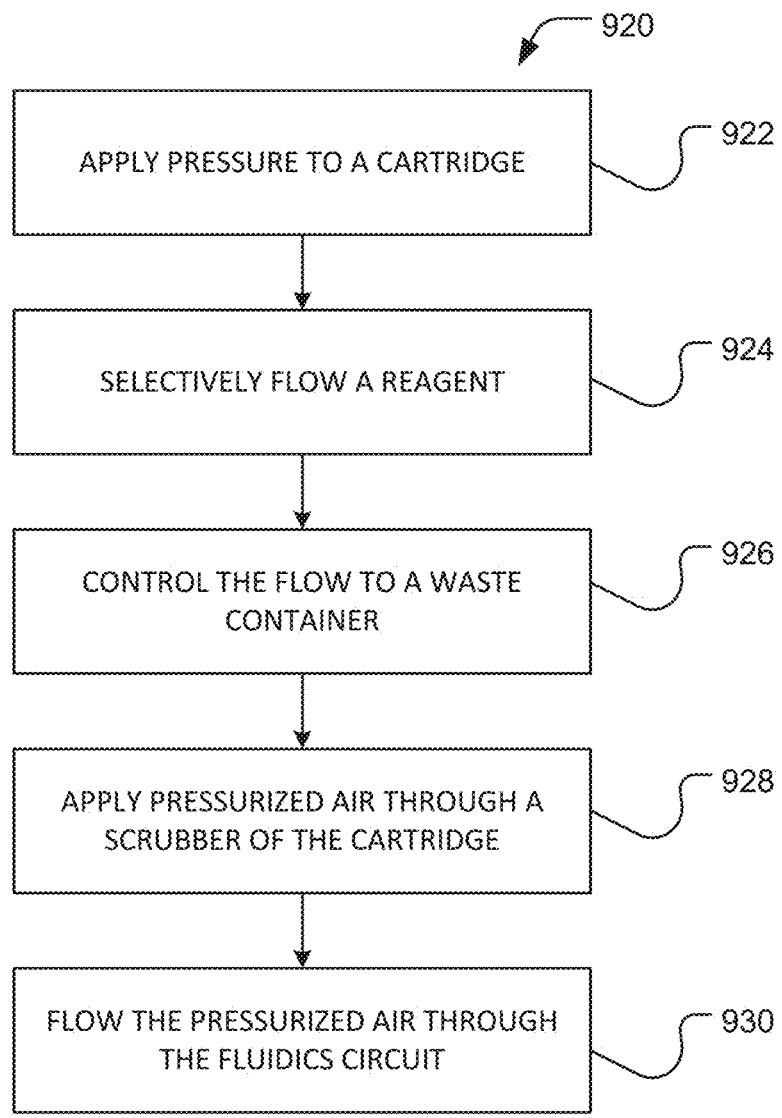
FIG. 27 includes a flow diagram of an example method for measuring an analyte.

FIG. 27 illustrates an exemplary method 920 for performing measurements of an analyte, followed by cleaning the system. For example, as illustrated at 922, pressure can be applied to a cartridge cavity, pressurizing reagent enclosures.

As illustrated at 924, reagents can selectively flow from the reagent enclosures by opening valves connecting individual reagent enclosures to the fluidic circuit. In particular, reagent can flow from select individual reagent enclosures in sequential orders, optionally separated by the flow of the wash solution from a separate container.

While the pressure of the cartridge cavity can provide a driving force for reagents from the reagent enclosures and individual reagent can be selected by selectively opening a valve associated with a reagent enclosure, the flow rate can be controlled, as illustrated 926, downstream of the fluidics circuit. In particular, flow can be controlled downstream of the fluidic circuit by controlling flow to the waste containers, for example, utilizing pinch flow regulators.

The system can then be clean by applying pressurized air through the scrubber of the cartridge, as illustrated 928, and flowing the pressurized scrubbed air through the fluidic circuit 930. The pressurized air can drive fluid from the fluidic circuit to the waste containers, for example through the sensor device and pinch flow regulators. In a further example, the pressurized air can drive reagent fluids backwards through their associated valves and into the reagent enclosures within the cartridge. In such a case, the cartridge cavity can be depressurized, allowing the pressurized air to drive the reagent fluids backwards into the reagent enclosures.

Figure 28:
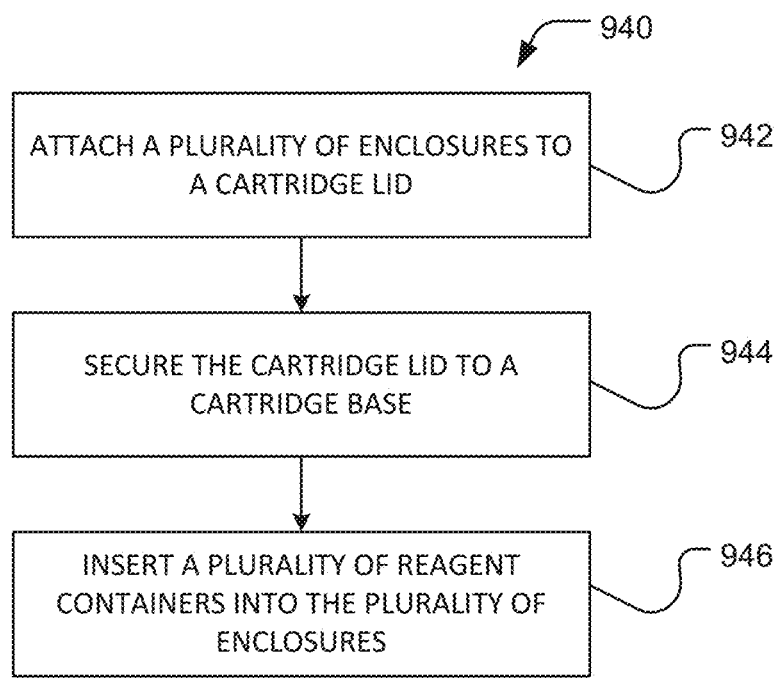
FIG. 28 includes a flow diagram of an example method for preparing a reagent cartridge.

As illustrated in FIG. 28, a method 940 for preparing a reagent cartridge includes attaching a plurality of reagent enclosures to a cartridge lid, as illustrated 942. An exemplary method is provided shown or illustrated in more detail in schematic of FIG. 17 and FIG. 18. The cartridge lid can be secured to a cartridge base, as illustrated 944, and a plurality of reagent containers can be inserted into the plurality of enclosures through the cartridge lid, as illustrated 946.

The system or instrument can be integrated into a process flow for sequencing. For example, the system can be utilized with the One Touch 2® or Ion Chef® systems, which perform template preparation. The instrument can be utilized for sequencing following the template preparation. The instrument is configurable to perform an initial analysis or can outsource the initial analysis and interpretation to a cloud or an external server.

The instrument can be configurable. For example, the system can include one or more central processing units, configurable amounts of RAM, upgradable graphics processing units and exchangeable storage including from 1 to 12 TB. The instrument is configured to receive and perform sequencing using different sequencing chips. Further, the system can be upgradable to access external servers for analysis and interpretation of the data received from the sequencing chip.

Multiple chips supported by the instrument can also support multiple assays, allowing for a different number of reads, read lengths, base outputs and applications. As such, the system is versatile and useful in a variety of fields of research.

Such a system is provided for desirable sequencing runs including output from a P1 proton chip including 19.6 Gb or a high accuracy run including 15.4 Gb.

In a first aspect, a method of preparing reagents includes inserting a cartridge into an instrument. The cartridge includes a plurality of reagent enclosures disposed in a cavity of the cartridge and exposing a port to an exterior of the cartridge. Each reagent enclosure includes a reagent container including a reagent and an internal cavity defining a compressible volume, an opening defined through the reagent container to the internal cavity. The method further includes connecting a plurality of fluid ports to the openings of the plurality of reagent enclosures; applying a solution through the fluid ports to at least partially fill the plurality of reagent enclosures; and cycling a pressure of the cavity, whereby for each of the reagent enclosures, during increasing pressure, the solution enters the internal cavity of the reagent container, combines with the reagent, and compresses the compressible volume, and during decreasing pressure, the compressible volume decreases and the reagent is ejected through the opening.

In an example of the first aspect, the method further includes pressurizing the cavity prior to applying the solution to remove gas from the plurality of enclosures.

In another example of the first aspect and the above examples, the reagent container further includes a compressible member disposed in the compressible volume.

In a further example of the first aspect and the above examples, the reagent includes a nucleotide.

In an additional example of the first aspect and the above examples, the method further includes sensing a position of the cartridge prior to connecting the plurality of fluid ports.

In another example of the first aspect and the above examples, the method further includes reading an identification tag of the cartridge with the instrument. For example, the method can further include connecting the plurality of fluid ports based on the reading.

In a further example of the first aspect and the above examples, the cartridge further includes a scrubber, the method further comprising connecting a gas system to the scrubber. For example, the scrubber is CO2 scrubber. In another example, cycling the pressure includes applying gas through the scrubber and into the cavity.

In a second aspect, a method of detecting an analyte with an instrument includes applying pressure to a cartridge coupled to an instrument. The cartridge includes a plurality of reagent enclosures disposed in a cavity of the cartridge and exposing a port to an exterior of the cartridge. Each reagent enclosure includes a reagent container including a reagent and an internal cavity defining a compressible volume, an opening defined through the reagent container to the internal cavity. The method further includes selectively flowing a reagent from a reagent enclosure of the plurality of reagent cartridges from the cartridge, through a fluidic circuit, a sensor, and a pinch flow regulator to a waste container; and controlling flow to the waste container using the pinch flow controller.

In an example of the second aspect, applying pressure to the cartridge includes flowing gas through a scrubber in the cartridge and into the cavity of the cartridge.

In another example of the second aspect and the above examples, the sensor includes a ion sensitive field effect transistor.

In a further example of the second aspect and the above examples, applying pressure includes compressing air with a compressor of the instrument.

In a third aspect, a method of cleaning an instrument includes applying pressurized air through a scrubber of a cartridge; and flowing the scrubbed pressurized air through a fluidics circuit, portions of the scrubbed pressurized air pushing a fluid through the fluidics circuit toward reagent enclosures of the cartridge and a portion through a sensor of the instrument through a pinch flow regulator to a waste container.

In a fourth aspect, a method for preparing a reagent cartridge includes attaching a plurality of enclosures to a cartridge lid; securing the cartridge lid to a cartridge base, the cartridge lid defining a plurality of openings, an opening of the cartridge lid providing access to an interior of an enclosure of the plurality of enclosures; and inserting a plurality of reagent containers into the plurality of enclosures, a reagent container of the plurality of reagent containers extending through the opening to the interior of the enclosure, the reagent container including a reagent and an internal cavity defining a compressible volume, an access defined through the reagent container to the internal cavity.

In an example of the fourth aspect, the reagent includes a nucleotide.

In another example of the fourth aspect and the above examples, the nucleotide is disposed on a porous material within the internal cavity of the reagent container.

In a further example of the fourth aspect and the above examples, the method further includes inserting a scrubber into the cartridge prior to securing the cartridge lid.

In a fifth aspect, a system includes a cartridge manifold to connect to a cartridge and provide fluidic communication between a plurality of reagent enclosures and a fluidics circuit and to provide fluidic communication between a compressed gas system, a cartridge cavity and a scrubber of the cartridge; the fluidics circuit; a sequencing device in fluidic communication with the fluidics circuit; a pinch flow regulator in fluidic communication with the sequencing device; and a waste container in fluidic communication with the pinch flow regulator.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of detecting an analyte with an instrument comprising a fluidic circuit, a sensor, and a pinch flow regulator, the method comprising:

applying pressure to a cartridge coupled to the instrument, the cartridge including a plurality of reagent enclosures disposed in one or more cavities of the cartridge, wherein the plurality of reagent enclosures include ports exposed to an exterior of the cartridge, and each reagent enclosure includes a reagent container, wherein the reagent container comprises an internal cavity defining a compressible volume, an opening defined through the reagent container to the internal cavity, and a reagent contained in the internal cavity;

selectively flowing the reagent from a reagent container of the plurality of reagent enclosures from the cartridge, through the fluidic circuit, the sensor, and the pinch flow regulator to a waste container, wherein the sensor outputs detection signals; and controlling flow to the waste container using the pinch flow regulator.

2. The method of claim 1, wherein applying pressure to the cartridge includes flowing gas through a scrubber in the cartridge and into the one or more cavities of the cartridge.

3. The method of claim 1, wherein the sensor includes an ion sensitive field effect transistor.

4. The method of claim 1, wherein applying pressure includes compressing air with a compressor of the instrument.

5. The method of claim 1, wherein applying pressure further comprises:

applying pressurized air through a scrubber of the cartridge; and flowing the pressurized air from the scrubber through the fluidic circuit, portions of the pressurized air flowed through the fluidic circuit pushing a fluid through the fluidic circuit toward the reagent enclosures of the cartridge.

6. The method of claim 1, further comprising:

applying pressurized air through a scrubber of the cartridge; and flowing the pressurized air from the scrubber through the fluidic circuit, portions of the pressurized air flowed through the fluidic circuit pushing a fluid through the sensor and through the pinch flow regulator to the waste container.

7. A method for preparing a reagent cartridge, the method comprising:

attaching a plurality of enclosures to a cartridge lid;

securing the cartridge lid to a cartridge base having one or more cartridge cavities, the cartridge lid defining a plurality of openings, an opening of the cartridge lid providing access to an interior of an enclosure of the plurality of enclosures; and inserting a plurality of reagent containers into the plurality of enclosures, a reagent container of the plurality of reagent containers extending through the opening of the cartridge lid to the interior of the enclosure, the reagent container including an internal cavity defining a compressible volume and a reagent contained in the internal cavity, the internal cavity being in fluid communication with an interior of the enclosure by an access defined through the reagent container.

8. The method of claim 7, wherein the reagent includes a nucleotide.

9. The method of claim 8, wherein the nucleotide is disposed on a porous material within the internal cavity of the reagent container.

10. The method of claim 7, further comprising inserting a scrubber into the cartridge base prior to securing the cartridge lid.

* * * * *

UNITED STATES PATENT AND TRADEMARK OFFICE
CERTIFICATE OF CORRECTION

PATENT NO. : 9,890,424 B2
APPLICATION NO. : 14/742404
DATED : February 13, 2018
INVENTOR(S) : Jonathan Schultz et al.

Page 1 of 1

It is certified that error appears in the above-identified patent and that said Letters Patent is hereby corrected as shown below:

In the Specification

Column 13, Line 45, should read as follows: --instance the diaphragm 3360 is to motivate the pinch--.

Column 13, Line 64, should read as follows: --the housing cover 3320 is controlled. In this manner, the--.

Column 15, Lines 64-65, should read as follows: --sure within the cartridge cavity and can then be cycled as illustrated at 916. Such cycling can cause mixing of--.

Signed and Sealed this
Fourth Day of December, 2018

Andrei Iancu
*Director of the United States Patent and Trademark Office*